United States Patent
Gono et al.

(10) Patent No.: US 8,279,275 B2
(45) Date of Patent: *Oct. 2, 2012

(54) SIGNAL PROCESSING DEVICE FOR BIOLOGICAL OBSERVATION APPARATUS

(75) Inventors: Kazuhiro Gono, Sagamihara (JP); Shoichi Amano, Hachioji (JP); Tomoya Takahashi, Hachioji (JP); Mutsumi Ohshima, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1312 days.

This patent is subject to a terminal disclaimer.

(21) Appl. No.: 11/914,180

(22) PCT Filed: Mar. 7, 2006

(86) PCT No.: PCT/JP2006/304385
§ 371 (c)(1),
(2), (4) Date: Dec. 13, 2007

(87) PCT Pub. No.: WO2006/120794
PCT Pub. Date: Nov. 16, 2006

(65) Prior Publication Data
US 2009/0058999 A1 Mar. 5, 2009

(30) Foreign Application Priority Data

May 11, 2005 (JP) ................................. 2005-138929
May 11, 2005 (JP) ................................. 2005-138930
May 13, 2005 (JP) ................................. 2005-141539

(51) Int. Cl.
A62B 1/04 (2006.01)
A61B 1/04 (2006.01)
(52) U.S. Cl. .............................. 348/65; 348/71; 600/109
(58) Field of Classification Search .................. 600/317, 600/109; 348/188, 65, 71
See application file for complete search history.

(56) References Cited

U.S. PATENT DOCUMENTS

| | | | | |
|---|---|---|---|---|
| 5,078,150 A * | 1/1992 | Hara et al. | ..................... | 600/476 |
| 5,331,551 A * | 7/1994 | Tsuruoka et al. | ............. | 382/128 |
| 5,408,263 A * | 4/1995 | Kikuchi et al. | ................. | 348/68 |
| 6,690,409 B1 * | 2/2004 | Takahashi | ....................... | 348/65 |
| 6,800,057 B2 * | 10/2004 | Tsujita et al. | ................. | 600/160 |
| 6,980,231 B1 * | 12/2005 | Ohsawa | ........................ | 348/188 |
| 2003/0028078 A1 * | 2/2003 | Glukhovsky | .................. | 600/109 |
| 2003/0158470 A1 * | 8/2003 | Wolters et al. | ................ | 600/317 |
| 2003/0176768 A1 * | 9/2003 | Gono et al. | ................... | 600/109 |
| 2004/0225185 A1 * | 11/2004 | Obata et al. | ................... | 600/118 |
| 2005/0096505 A1 * | 5/2005 | Imaizumi et al. | ............. | 600/180 |
| 2007/0232861 A1 * | 10/2007 | Kohno et al. | ................. | 600/160 |

FOREIGN PATENT DOCUMENTS

EP 1 302 152 A1 4/2003

(Continued)

OTHER PUBLICATIONS

Extended Supplementary European Search Report dated Mar. 29, 2010.

Primary Examiner — Firmin Backer
Assistant Examiner — Michael A Chambers
(74) Attorney, Agent, or Firm — Scully, Scott, Murphy & Presser, P.C.

(57) ABSTRACT

Tissue information of a desired deep portion of a biological tissue based on a spectral image obtained from signal processing is adjusted to image information in a color tone suitable for observation. Outputs of a matrix computing section 436 are respectively connected to integrating sections 438a to 438c, and after integrating computation is performed for them, color conversion computation is performed for respective spectral image signals ΣF1 to ΣF3 in a color adjusting section 440, spectral color channel image signals Rch, Gch and Bch are created from the spectral image signals ΣF1 to ΣF3, and images of the spectral color channel images Rch, Gch and Bch are sent to a display monitor 106 via a switching section 439.

31 Claims, 28 Drawing Sheets

FOREIGN PATENT DOCUMENTS

| | | |
|---|---|---|
| JP | 9-292575 | 11/1997 |
| JP | 2002-034908 | 2/2002 |
| JP | 2002-095635 | 4/2002 |
| JP | 2002-233501 | 8/2002 |
| JP | 2002-267949 | 9/2002 |
| JP | 2003-093336 | 4/2003 |
| JP | 2003-180632 | 7/2003 |
| JP | 2004-77143 | 3/2004 |
| JP | 2004-237081 | 8/2004 |
| JP | 2005-074034 | 3/2005 |
| WO | WO 02/07588 A1 | 1/2002 |

\* cited by examiner

| R | G | R | G |
|---|---|---|---|
| R | B | R | B |
| R | G | R | G |
| R | B | R | B |

FIG.30
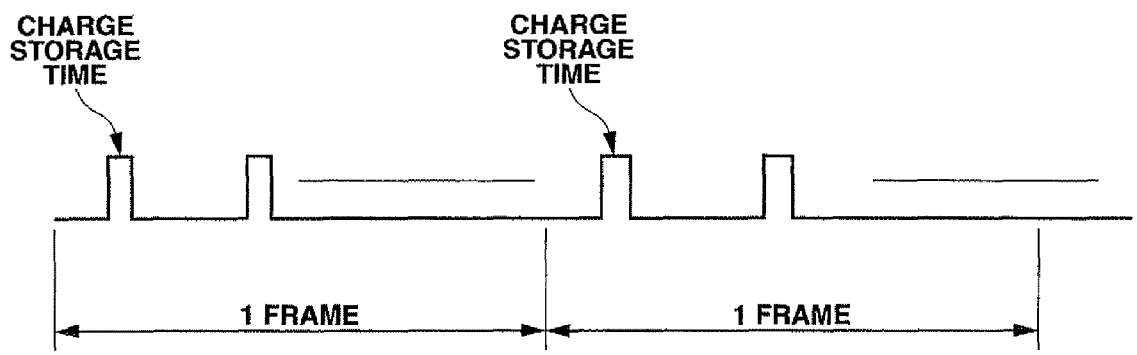
FIG.31
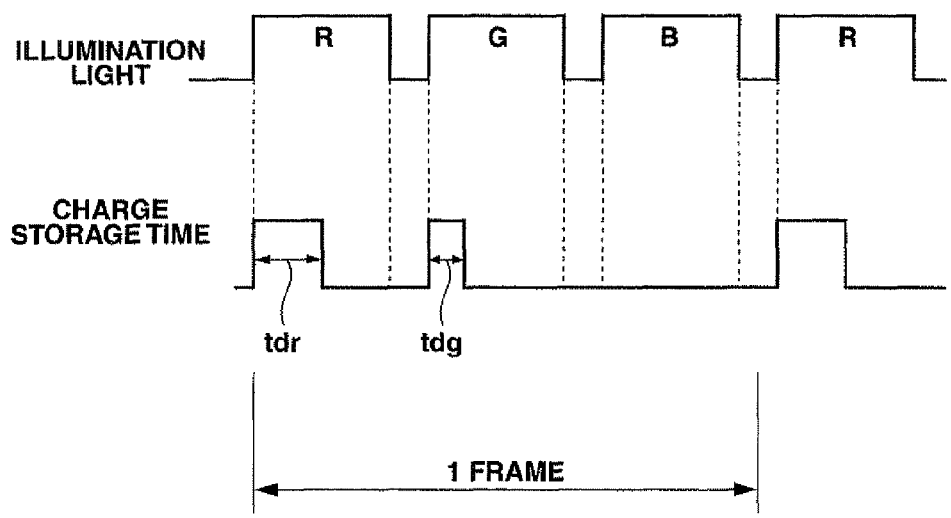
FIG.32
| Mg | G | Mg | G |
| --- | --- | --- | --- |
| Cy | Ye | Cy | Ye |
| G | Mg | G | Mg |
| Cy | Ye | Cy | Ye |

FIG.51
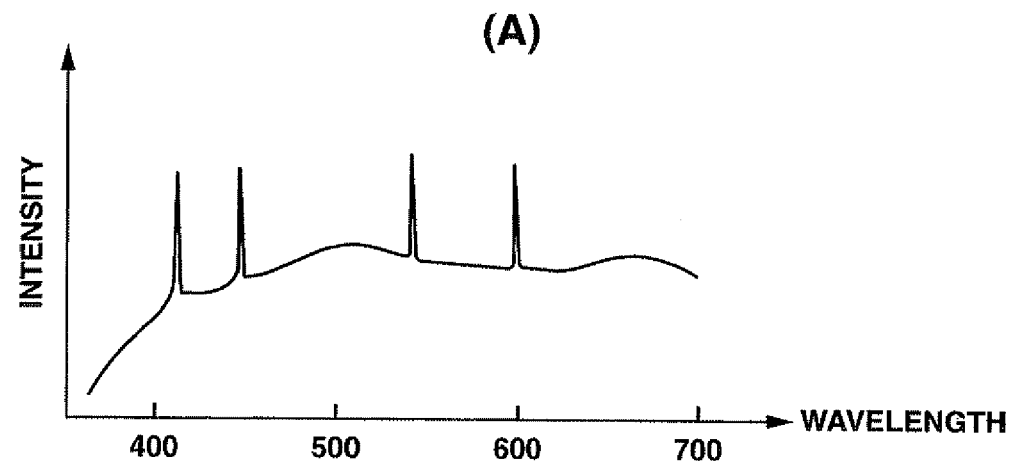
(A)
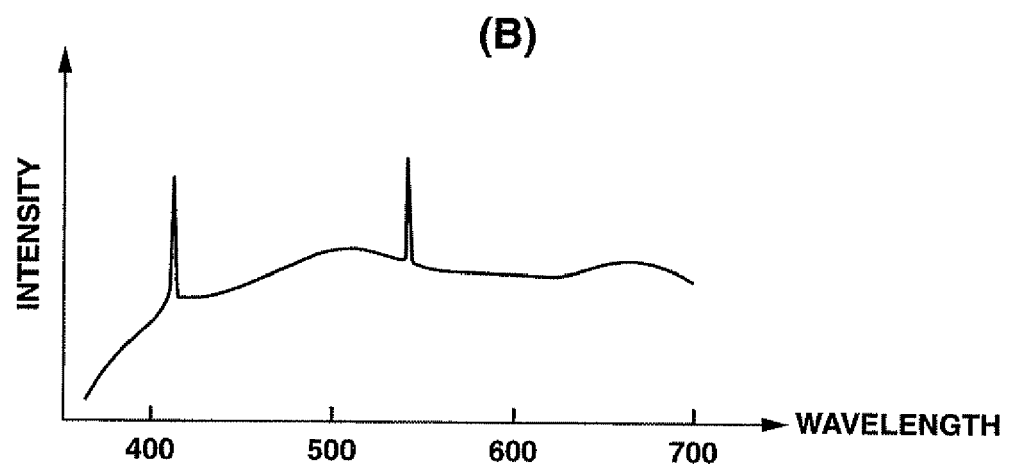
(B)
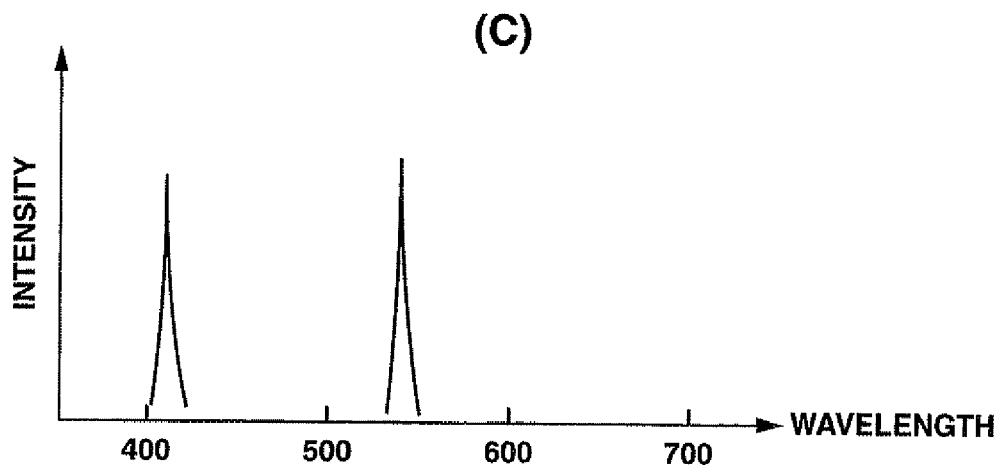
(C)

SIGNAL PROCESSING DEVICE FOR BIOLOGICAL OBSERVATION APPARATUS

TECHNICAL FIELD

The present invention relates to a signal processing device for a biological observation apparatus which uses a color image signal obtained by picking up an image of a living body and displays the image on a monitor as a spectral image by signal processing.

BACKGROUND ART

Conventionally, as a biological observation apparatus, an endoscope apparatus which irradiates illumination light and obtains an endoscope image in a body cavity has been widely used. In an endoscope apparatus of this kind, an electronic endoscope having image pick up means which guides illumination light from a light source into a body cavity by using a light guide or the like and picks up an image of a subject by its feedback light, and by performing signal processing of an image pickup signal from the image pickup means by a video processor, the endoscope image is displayed on an observation monitor so that an observation region of a patient or the like is observed.

When ordinary biological tissue observation is performed in an endoscope apparatus, in one method, white light in a visible light region is emitted with a light source device, frame sequential light is irradiated to a subject via a revolving filter of R, G, B and the like, for example, feedback light by the frame sequential light is synchronized by a video processor and is subjected to image processing, whereby a color image is obtained. When ordinary biological tissue observation is performed in an endoscope apparatus, in another method, color chips are distributed to a front surface of an image pickup surface of image pickup means of an endoscope, white light in a visible light region is emitted with a light source device, an image is picked up by separating feedback light by the white light in accordance with color components with the color chips, and image processing is performed with a video processor, whereby a color image is obtained.

Since a biological tissue differs in light absorption characteristic and scattering characteristic depending on the wavelength of irradiated light, for example, Japanese Patent Laid-Open No. 2002-95635 discloses a narrow band light endoscope apparatus which irradiates a biological tissue with illumination light in a visible light region and narrow band RGB sequential light with discrete spectral characteristics, and obtains tissue information of a desired deep portion of the biological tissue.

Japanese Patent Laid-Open No. 2003-93336 discloses an electronic endoscope apparatus which applies signal processing to an image signal by illumination light in a visible light region to create a discrete spectral image, and obtains image information of a biological tissue.

However, for example, in the apparatus disclosed in the above described Japanese Patent Laid-Open No. 2003-93336, an spectral image is obtained by signal processing, and a filter for generating narrow band RGB light is not required, but since the obtained spectral image is simply outputted to a monitor, there arises a fear that the image displayed on the monitor does not become an image of a color tone suitable for observation of tissue information of a desired deep portion of a biological tissue.

In the apparatus disclosed in Japanese Patent Laid-Open No. 2002-95635, an optically narrow band bandpass filter is used. However, in the apparatus disclosed in Japanese Patent Laid-Open No. 2003-93336, a narrow band spectral image signal (also called a spectral signal) is created by signal processing without using an optically narrow band filter.

However, in the apparatus disclosed in Japanese Patent Laid-Open No. 2003-93336, processing of creating a spectral signal which is obtained in the case of using a narrow-band bandpass filter is performed by electrical computation processing by matrix computation from a color image signal (corresponding to a quasi-bandpass filter) picked up in a wide wavelength band without using an optically narrow band bandpass filter, and therefore, the spectral characteristic of illumination light which is generated with a light source and irradiated to a biological tissue has a large influence, but the prior art example only discloses the use of only one lamp.

Therefore, there is a disadvantage of securing precision or reliability of a spectral signal electrically generated.

The present invention is made in view of the above described circumstances, and has an object to provide a signal processing device for a biological observation apparatus which can adjust tissue information of a desired deep portion of a biological tissue based on a spectral image obtained by signal processing to image information in a color tone suitable for observation.

Further, the present invention has an object to provide a biological observation apparatus including a function of electrically creating a spectral signal from a biological signal, and suitable for obtaining a spectral signal with higher precision or reliability.

DISCLOSURE OF INVENTION

Means for Solving the Problem

A signal processing device for a biological observation apparatus according to a first aspect of the present invention is a signal processing device for a biological observation apparatus comprising an illumination unit for irradiating light to a living body that is a test subject, and/or a signal processing control unit for photoelectrically converting light reflected from the living body based on illumination light from the illumination unit, controlling an operation of an image pickup unit creating an image pickup signal, and outputting the image pickup signal to a display device, and comprises a spectral signal creating section for creating a spectral signal corresponding to an image in a narrow band of an optical wavelength from the image pickup signal by signal processing, and a color adjusting section for adjusting a color tone for each of a plurality of bands forming the spectral signal when outputting the spectral signal to the display device.

A biological observation apparatus according to a second aspect of the present invention has, in a biological observation apparatus photoelectrically converting light reflected from a living body based on illumination light irradiated to the living body that is a test subject, controlling an operation of an image pickup unit creating an image pickup signal in a wide band, and outputting the image pickup signal to a display device, a spectral signal creating section for creating a spectral signal corresponding to an image in a narrow band of an optical wavelength from the image pickup signal by signal processing, a color adjusting section for adjusting a color tone for each of a plurality of bands forming the spectral signal when outputting the spectral signal to the display device, and a plurality of light sources for emitting a plurality of illumi-

BRIEF DESCRIPTION OF THE DRAWINGS

FIG. 30 is a diagram showing charge storage time of a CCD of FIG. 29;

FIG. 31 is a diagram showing charge storage time of a CCD according to an embodiment 5 of the present invention;

FIG. 32 is a diagram showing arrangement of color filters according to an embodiment 6 of the present invention;

FIG. 51 is a diagram showing light emission characteristic examples of illumination light at the time of the spectral image observation mode in the modified example of the embodiment 9.

BEST MODE FOR CARRYING OUT THE INVENTION

Embodiments of the present invention will be described hereinafter with reference to the drawings.

Embodiment 1

Figure 1:
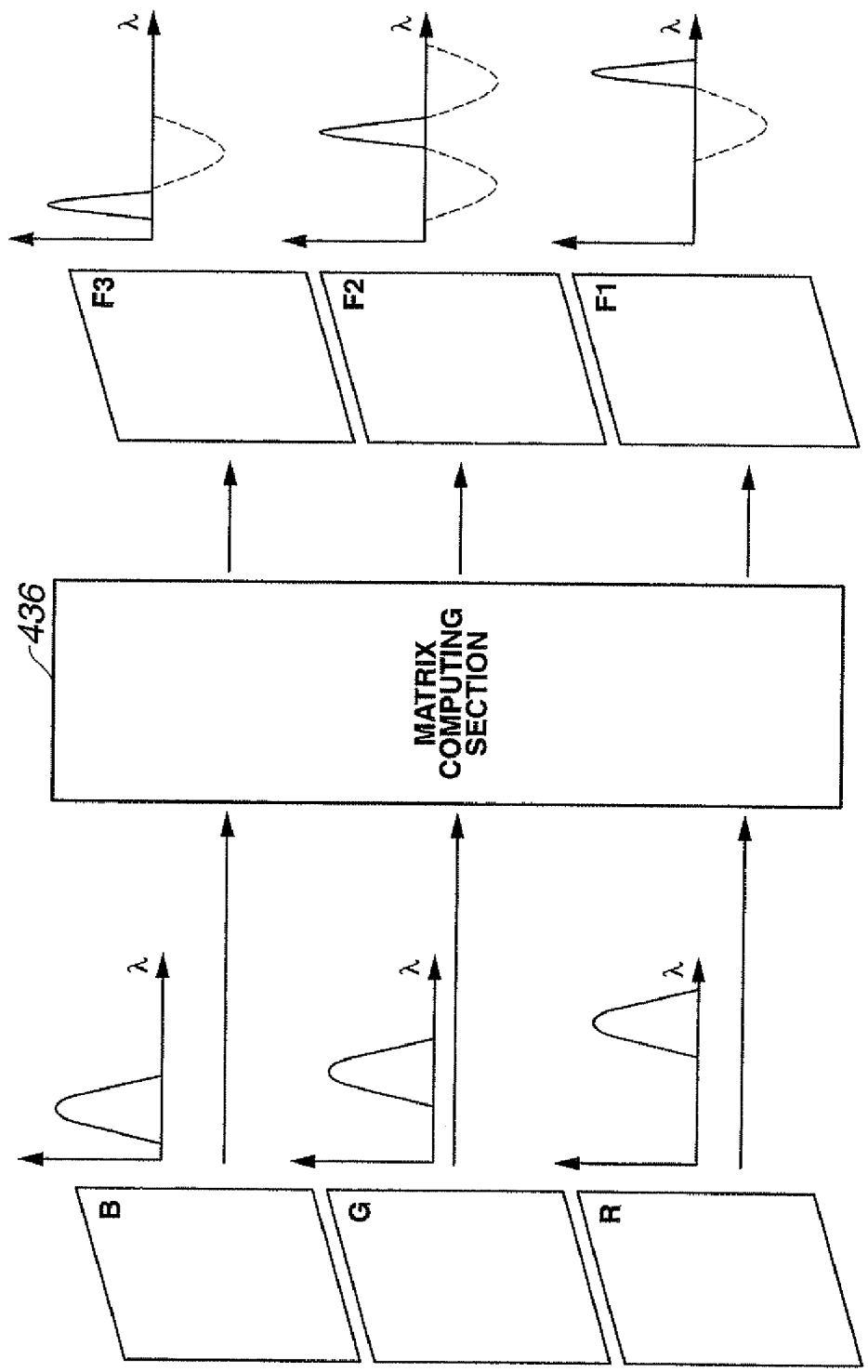
FIG. 1 is a conceptual diagram showing a flow of a signal when creating a spectral image signal from a color image signal according to an embodiment 1 of the present invention.
Figure 2:
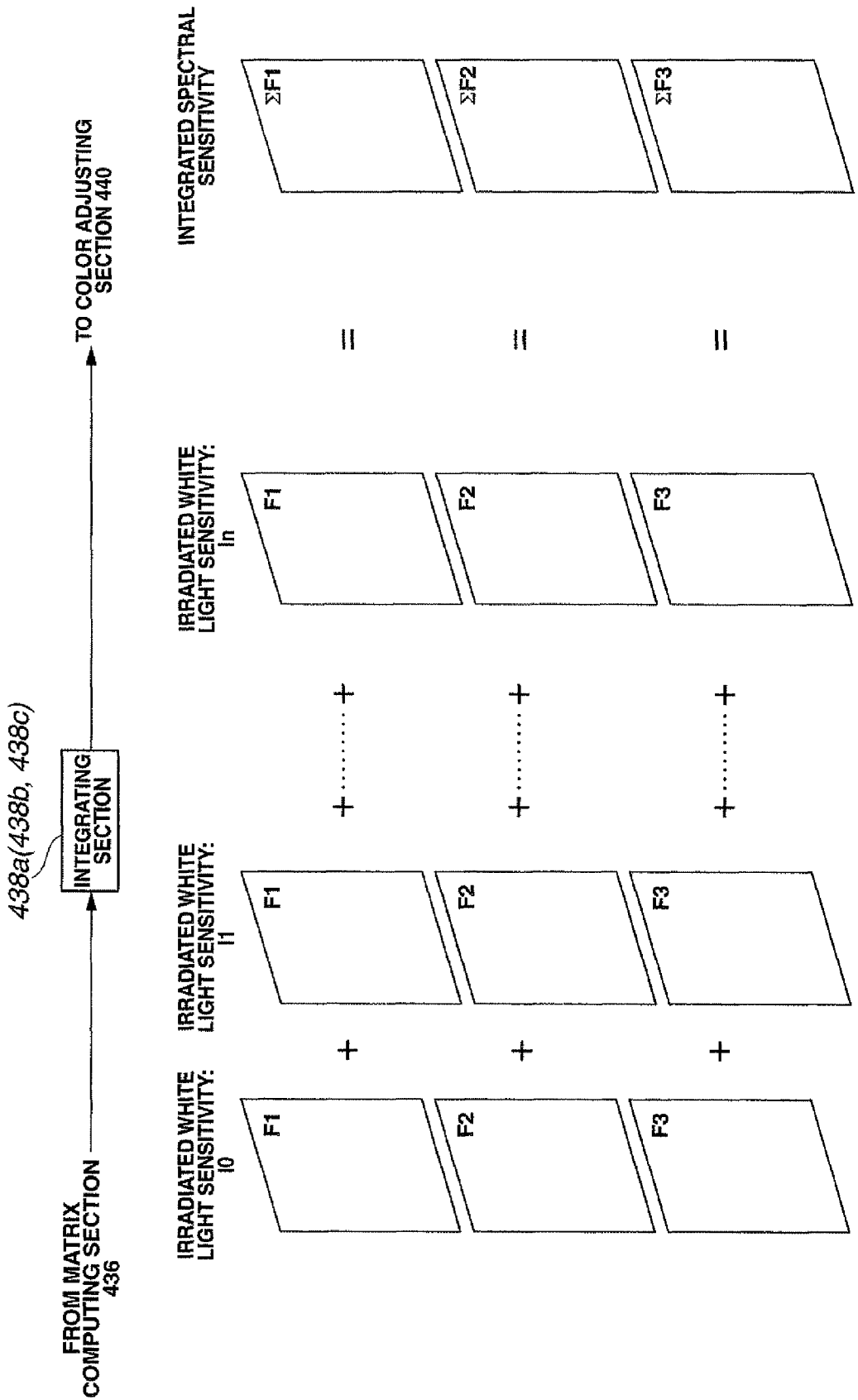
FIG. 2 is a conceptual diagram showing integrating computation of the spectral image signal according to the embodiment 1 of the present invention.
Figure 3:
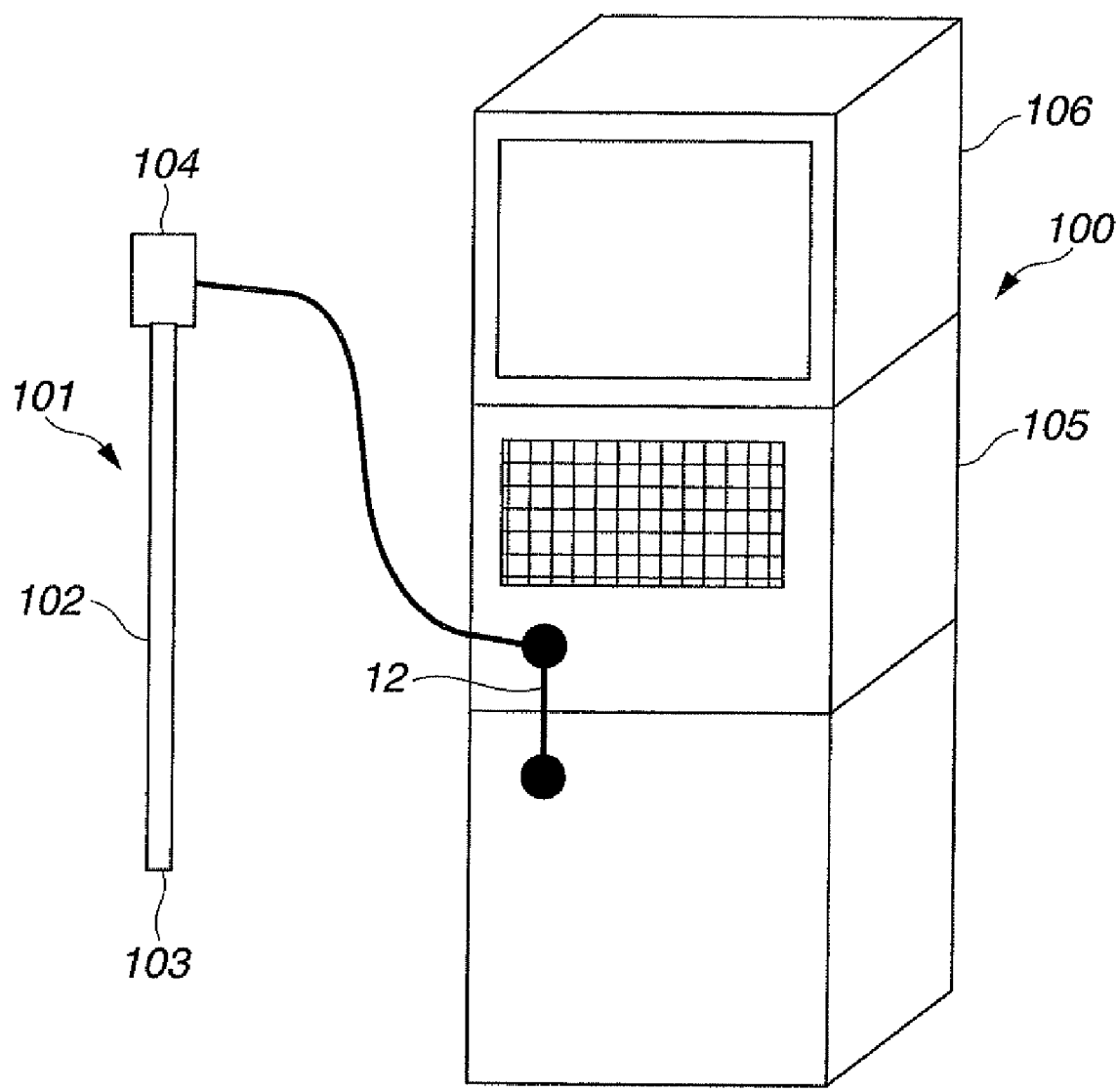
FIG. 3 is an exterior view showing an appearance of an electronic endoscope apparatus according to the embodiment 1 of the present invention.
Figure 4:
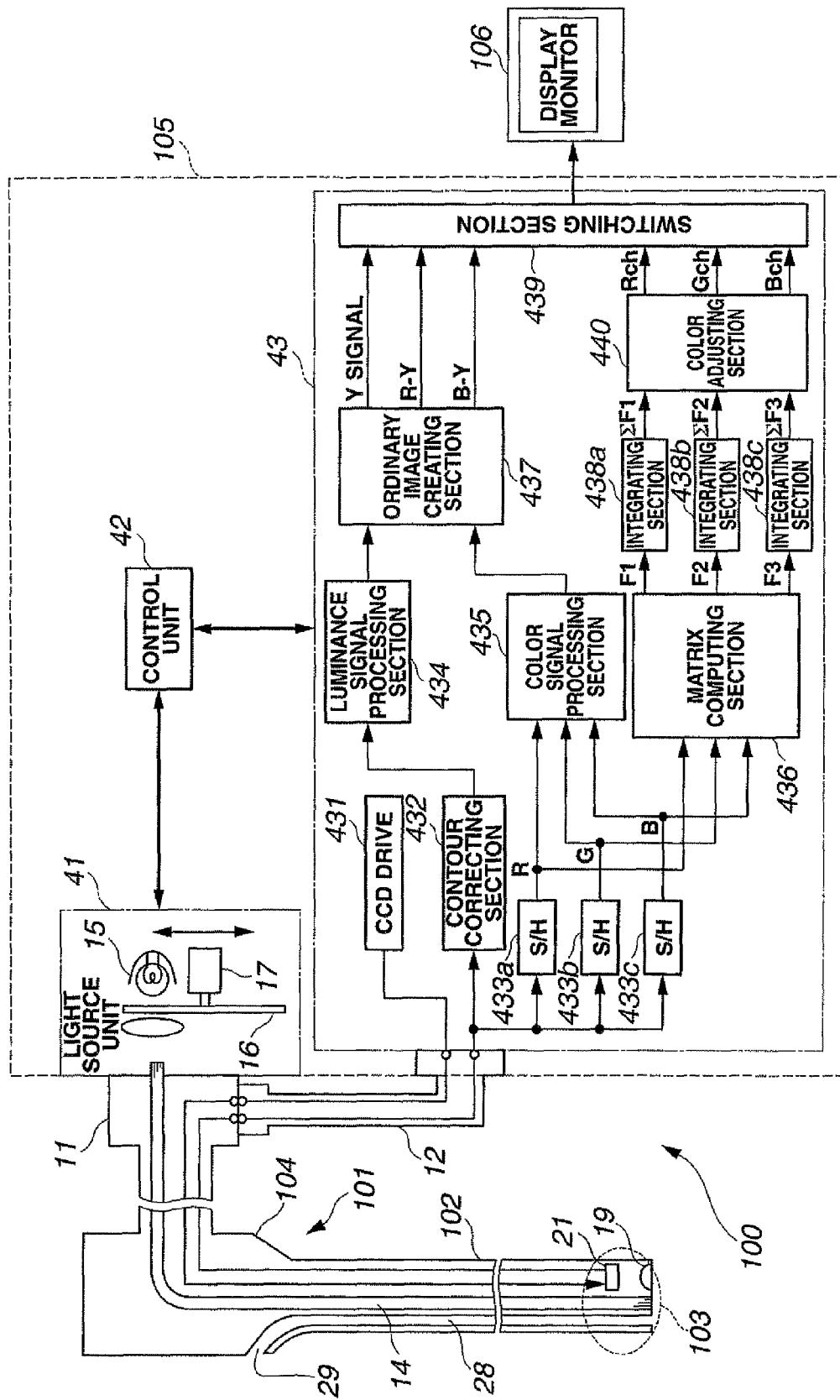
FIG. 4 is a block diagram showing a configuration of the electronic endoscope apparatus of FIG. 3.
Figures 5, 6:
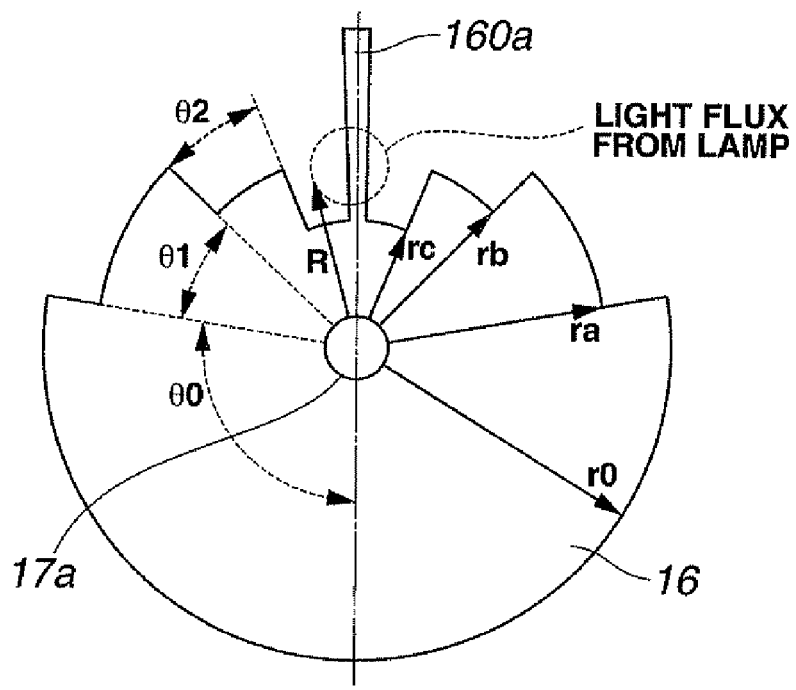
FIG. 5 is an exterior view showing an appearance of a chopper of FIG. 4.
FIG. 6 is a diagram showing an arrangement of color filters disposed on an image pickup surface of a CCD of FIG. 3.
Figure 7:
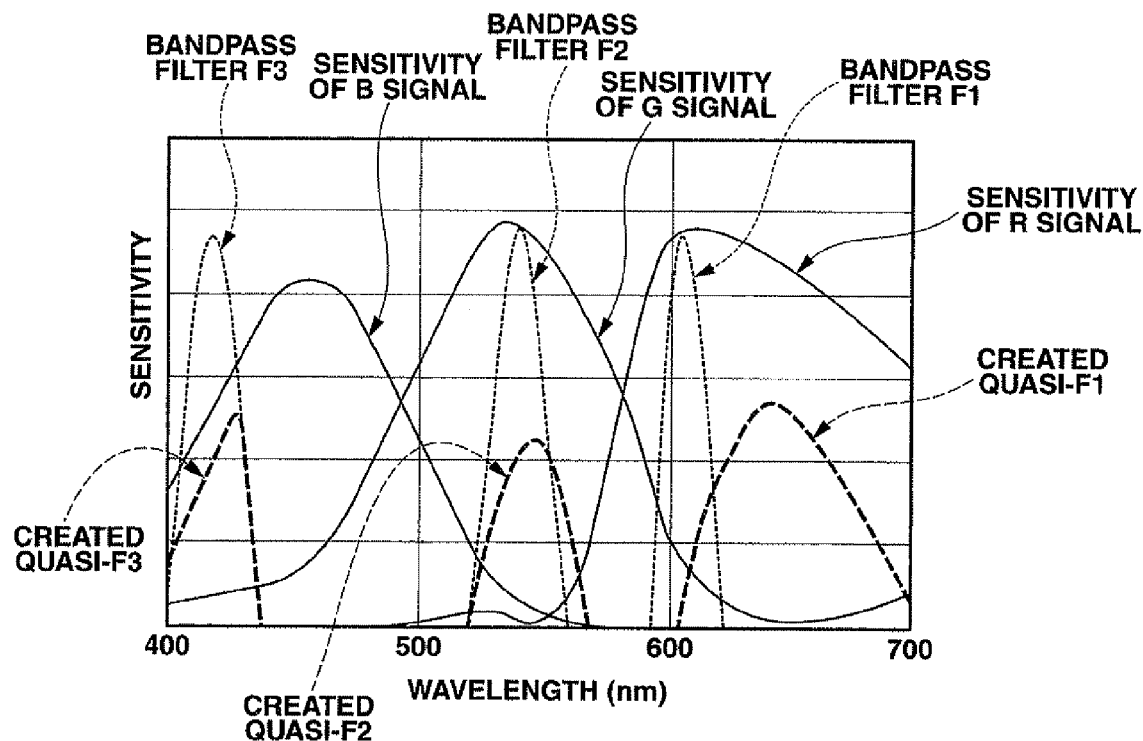
FIG. 7 is a diagram showing spectral sensitivity characteristics of the color filters of FIG. 6.
Figure 8:
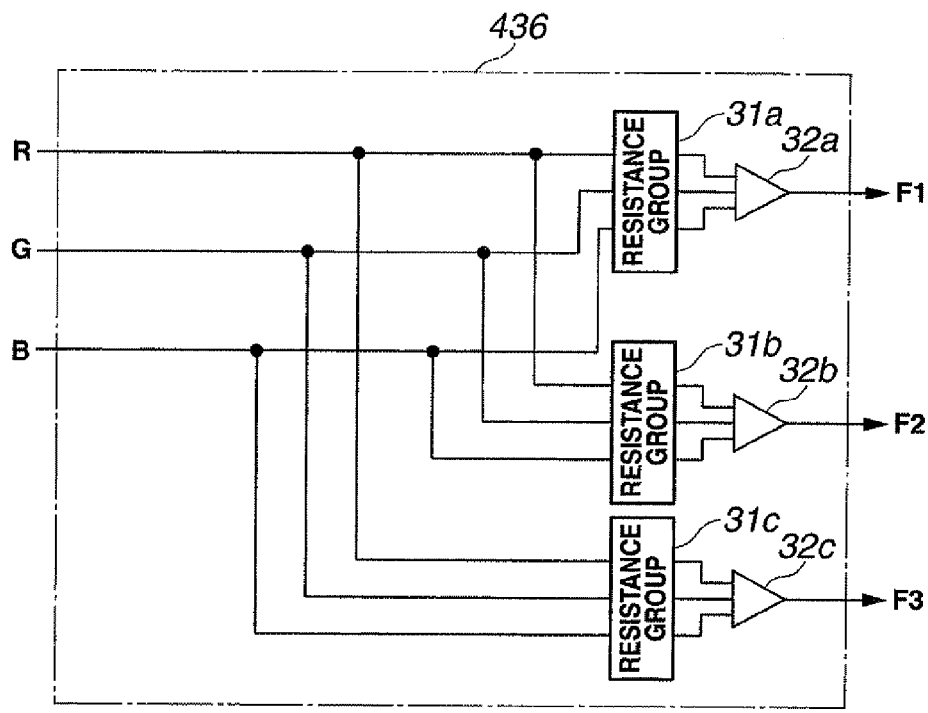
FIG. 8 is a configuration diagram showing a configuration of a matrix computing section of FIG. 4.
Figure 9:
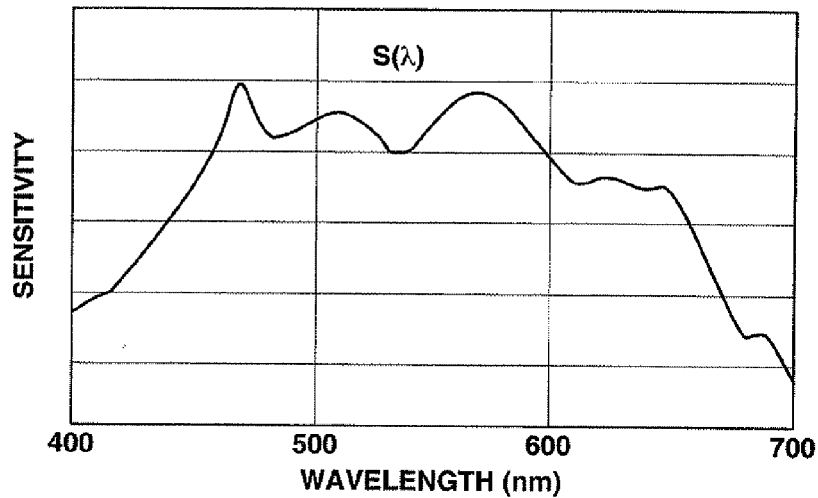
FIG. 9 is a spectrum diagram showing a spectrum of a light source according to the embodiment 1 of the present invention.
Figure 10:
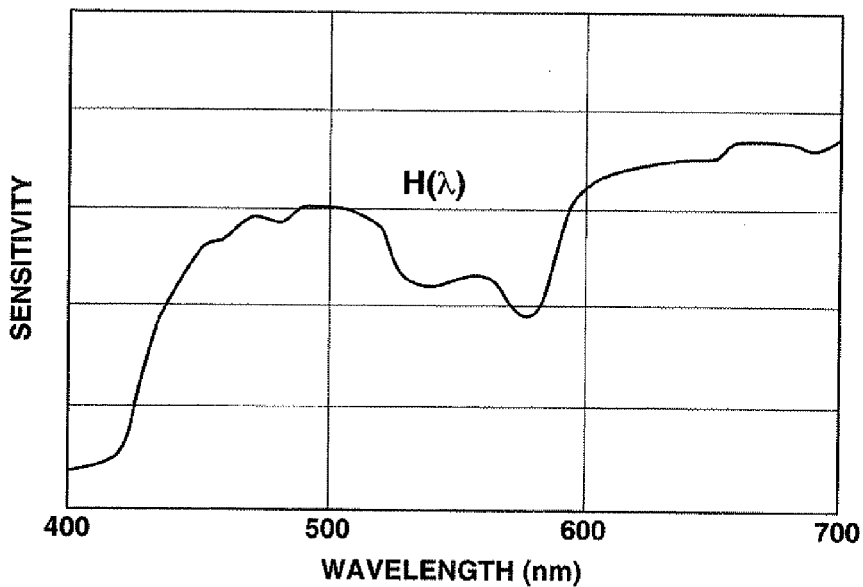
FIG. 10 is a spectrum diagram showing a reflection spectrum of a living body according to the embodiment 1 of the present invention.

FIGS. 1 to 26 relate to an embodiment 1 of the present invention. FIG. 1 is a conceptual diagram showing a flow of a signal when creating a spectral image signal from a color image signal. FIG. 2 is a conceptual diagram showing integrating computation of the spectral image signal. FIG. 3 is an exterior view showing an appearance of an electronic endoscope apparatus. FIG. 4 is a block diagram showing a configuration of the electronic endoscope apparatus of FIG. 3. FIG. 5 is an exterior view showing an appearance of a chopper of FIG. 4. FIG. 6 is a diagram showing an arrangement of color filters disposed on an image pickup surface of a CCD of FIG. 3. FIG. 7 is a diagram showing spectral sensitivity characteristics of the color filters of FIG. 6. FIG. 8 is a configuration diagram showing a configuration of a matrix computing section of FIG. 4. FIG. 9 is a spectrum diagram showing a spectrum of a light source. FIG. 10 is a spectrum diagram showing a reflection spectrum of a living body.

Figure 11:
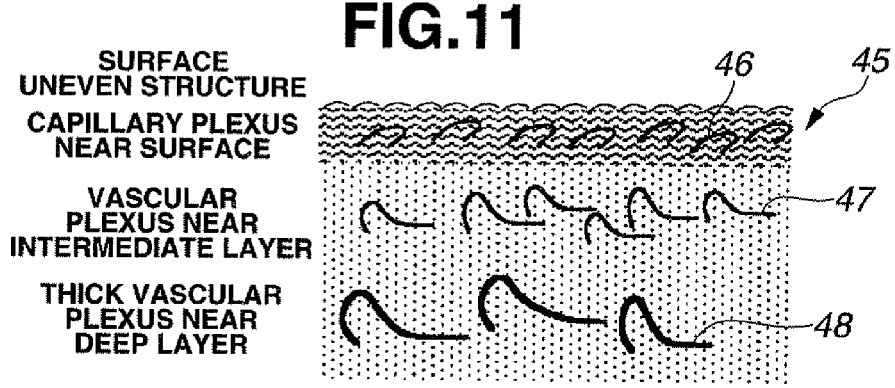
FIG. 11 is a view showing a structure in a layer direction of a biological tissue to be observed by the electronic endoscope apparatus of FIG. 4.
Figure 12:
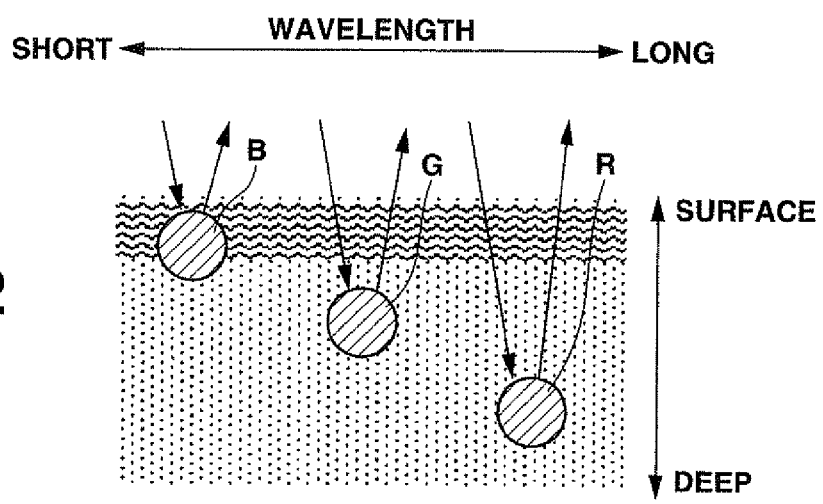
FIG. 12 is a view explaining a reaching state of illumination light from the electronic endoscope apparatus of FIG. 4 in the layer direction of the biological tissue.
Figure 13:
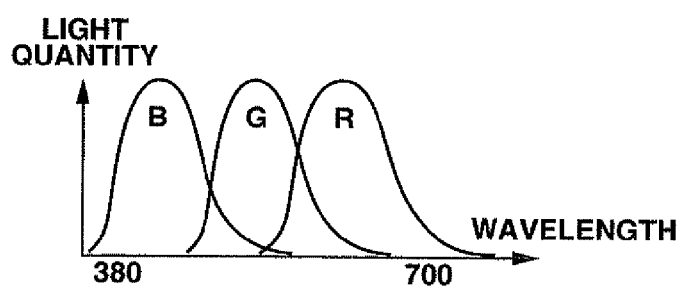
FIG. 13 is a diagram showing a spectral characteristic of each band of white light.
Figure 14:
FIG. 14 is a first diagram showing each band image by the white light of FIG. 13.
Figure 15:
FIG. 15 is a second diagram showing each band image by the white light of FIG. 13.
Figure 16:
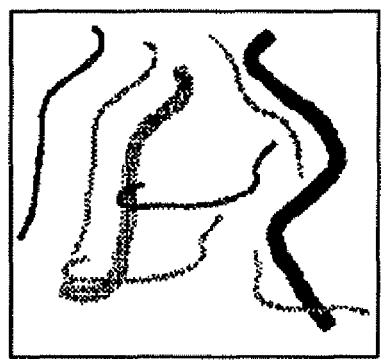
FIG. 16 is a third view showing each band image by the white light of FIG. 13.
Figure 17:
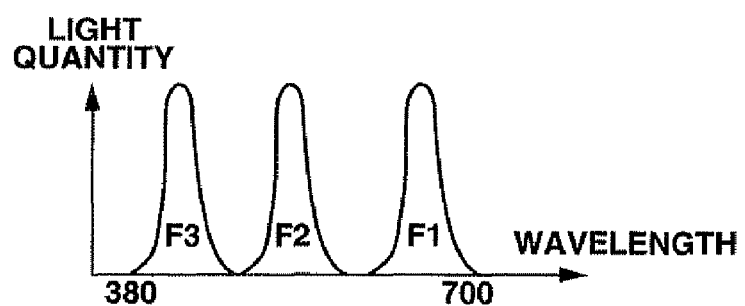
FIG. 17 is a diagram showing spectral characteristics of spectral images created by the matrix computing section of FIG. 8.
Figure 18:
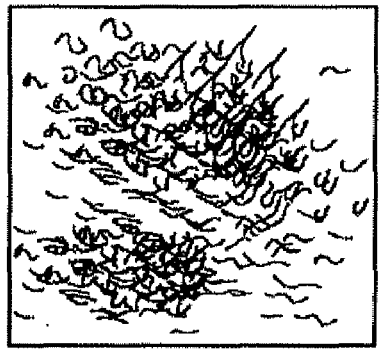
FIG. 18 is a first diagram showing each of the spectral images of FIG. 17.
Figure 19:
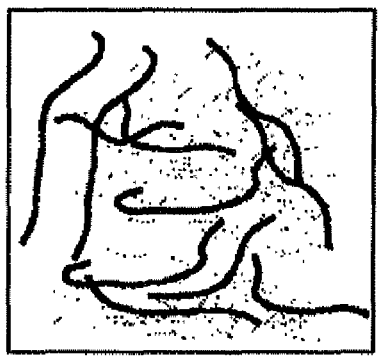
FIG. 19 is a second diagram showing each of the spectral images of FIG. 17.
Figure 20:
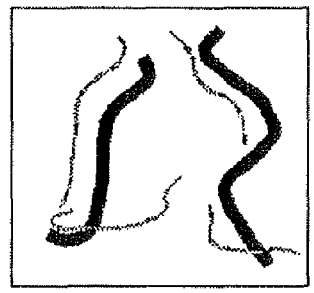
FIG. 20 is a third diagram showing each of the spectral images of FIG. 17.

FIG. 11 is a view showing a structure in a layer direction of a biological tissue to be observed by the electronic endoscope apparatus of FIG. 4. FIG. 12 is a view explaining a reaching state of illumination light from the electronic endoscope apparatus of FIG. 4 in the layer direction of the biological tissue. FIG. 13 is a diagram showing a spectral characteristic of each band of white light. FIG. 14 is a first diagram showing each band image by the white light of FIG. 13. FIG. 15 is a second diagram showing each band image by the white light of FIG. 13. FIG. 16 is a third view showing each band image by the white light of FIG. 13. FIG. 17 is a diagram showing spectral characteristics of spectral images created by the matrix computing section of FIG. 8. FIG. 18 is a first diagram showing each of the spectral images of FIG. 17. FIG. 19 is a second diagram showing each of the spectral images of FIG. 17. FIG. 20 is a third diagram showing each of the spectral images of FIG. 17.

Figure 21:
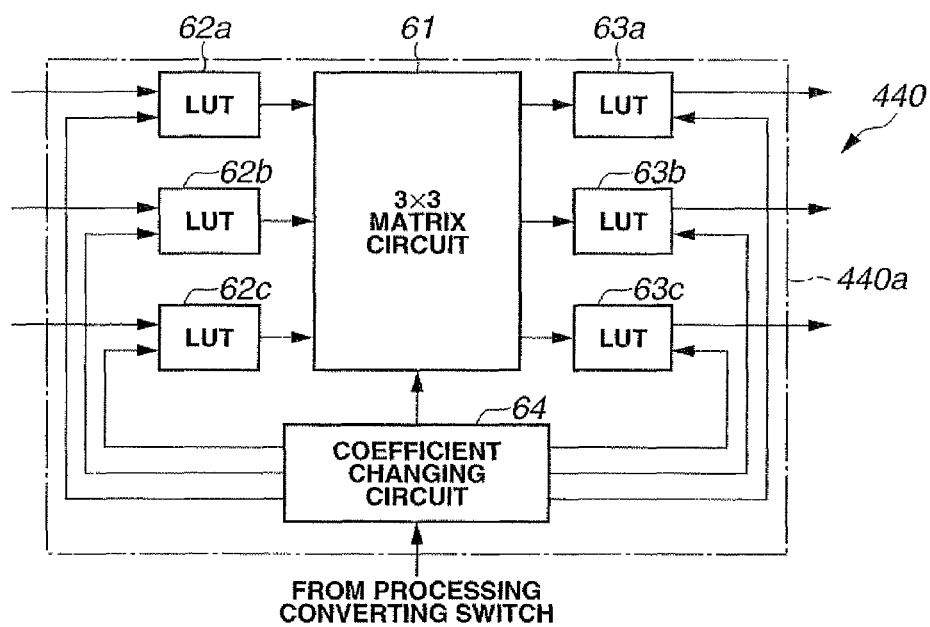
FIG. 21 is a block diagram showing a configuration of a color adjusting section of FIG. 4.
Figure 22:
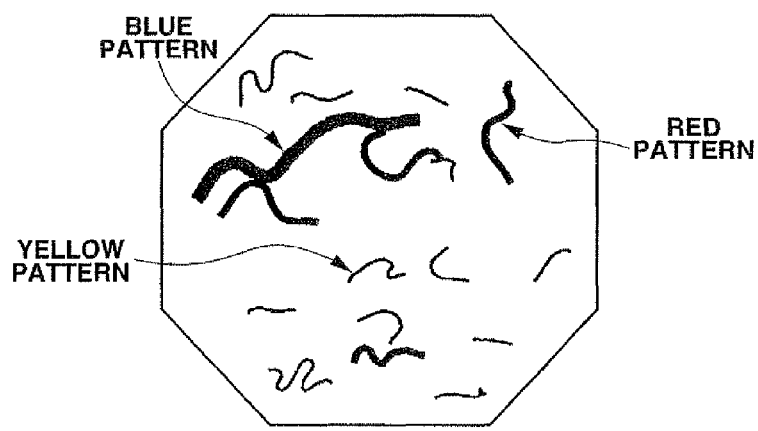
FIG. 22 is a diagram explaining an operation of the color adjusting section of FIG. 21.
Figure 23:
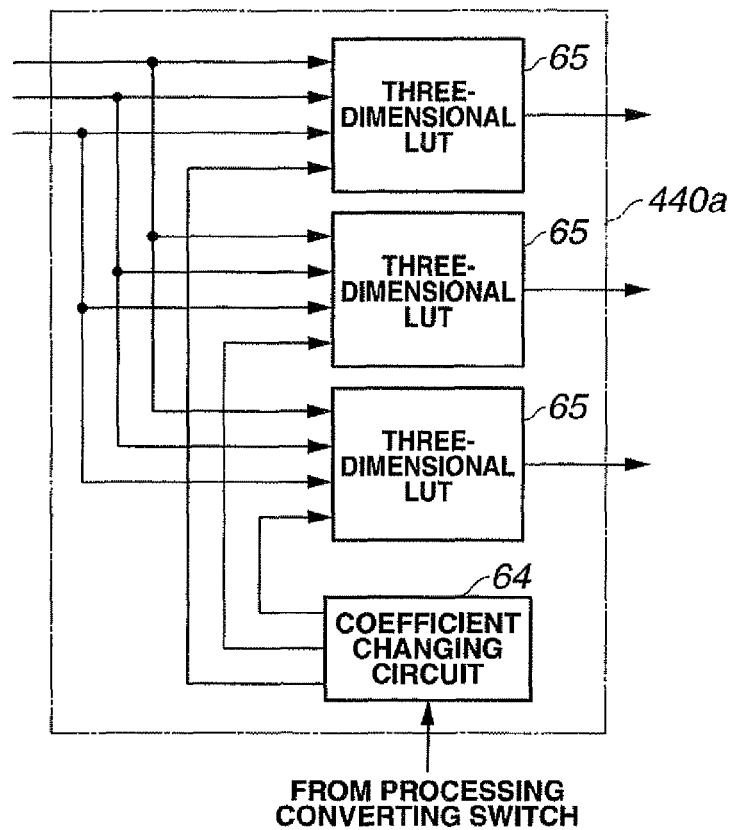
FIG. 23 is a block diagram showing a configuration of a modified example of the color adjusting section of FIG. 4.
Figure 24:
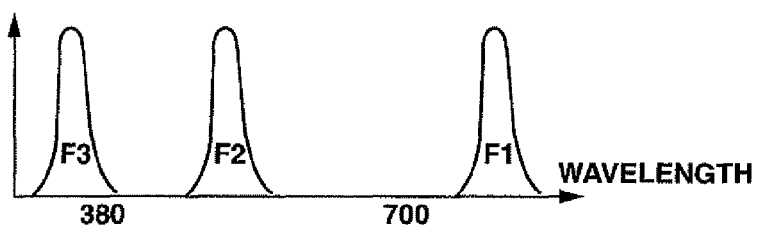
FIG. 24 is a diagram showing spectral characteristics of the first modified example of the spectral images of FIG. 17.
Figure 25:
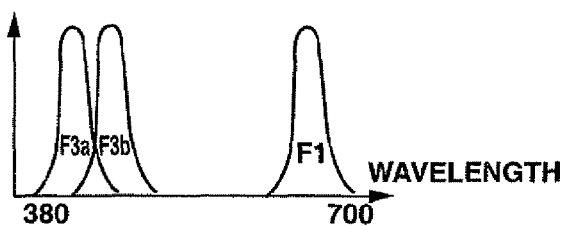
FIG. 25 is a diagram showing spectral characteristics of a second modified example of the spectral images of FIG. 17.
Figure 26:
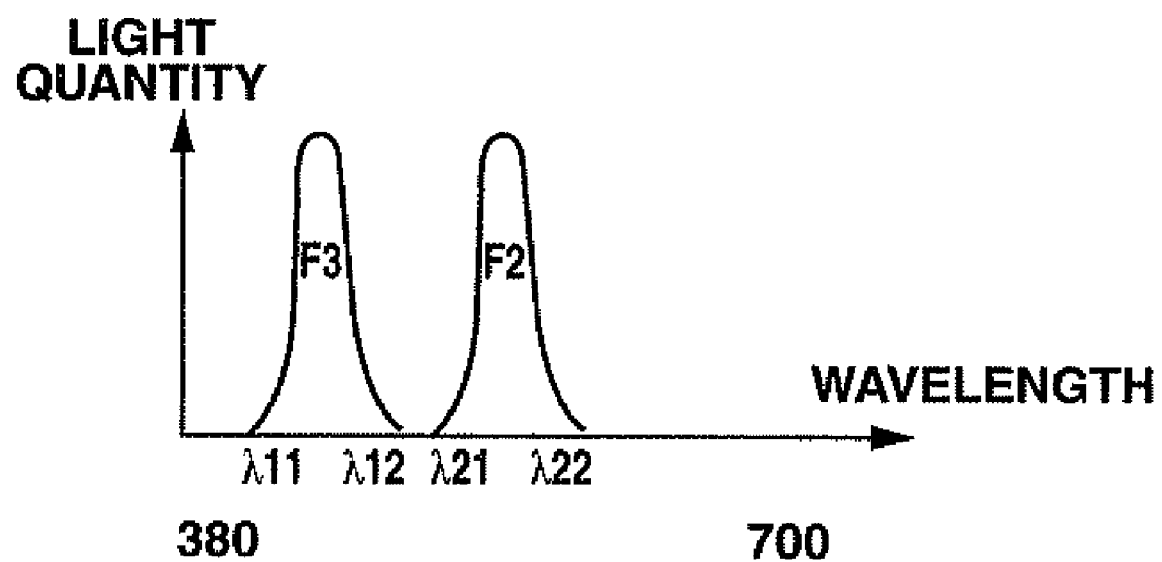
FIG. 26 is a diagram showing spectral characteristics of a third modified example of the spectral images of FIG. 17.

FIG. 21 is a block diagram showing a configuration of a color adjusting section of FIG. 4. FIG. 22 is a diagram explaining an operation of the color adjusting section of FIG. 21. FIG. 23 is a block diagram showing a configuration of a modified example of the color adjusting section of FIG. 4. FIG. 24 is a diagram showing spectral characteristics of the first modified example of the spectral images of FIG. 17. FIG. 25 is a diagram showing spectral characteristics of a second modified example of the spectral images of FIG. 17. FIG. 26 is a diagram showing spectral characteristics of a third modified example of the spectral images of FIG. 17.

In an electronic endoscope apparatus as a biological observation apparatus in the embodiment of the present invention, light is irradiated to a living body that is a test subject from an illuminating light source, and light which is reflected from the living body based on the irradiated light is received by a solid state image pickup element which is an image pickup unit and is subjected to photoelectric conversion, whereby an image pickup signal that is a color image signal is created, and from the image pickup signal, a spectral image signal that is a spectral signal corresponding to an image in an optical wavelength narrow band is created by signal processing.

Before describing the embodiment 1 according to the present invention, a matrix calculating method which is a basis of the present invention will be described hereinafter. Here, the matrix means a predetermined coefficient which is used when creating a spectral image signal as a spectral signal from a color image signal obtained for creating a color image (hereinafter, also called an ordinary image).

Following the description of the matrix, a correction method for obtaining a more accurate spectral image signal, a method for improving S/N which improves an S/N ratio of the created spectral image signal will be described. The correction method, the method for improving S/N can be used in accordance with necessity. Hereinafter, vectors and matrixes will be expressed by bold letters or quotation marks (for example, a matrix A is expressed by "a bold letter A" or "A"), and the other words will be expressed without letter decoration.

(Matrix Calculating Method)

FIG. 1 is a conceptual diagram showing a flow of a signal when creating a spectral image signal equivalent to an image corresponding to an image in a narrower optical wavelength band from a color image signal (in this case, in order to simplify the explanation, R, G and B are adopted, but the combination of G, Cy, Mg and Ye may be adopted in a complementary color type solid state image pickup element).

First, the electronic endoscope apparatus converts color sensitivity characteristics as spectral sensitivity characteristics of image pickup units of R, G and B into numeric data. In this case, the color sensitivity characteristics of R, G and B are characteristics of output to wavelengths respectively obtained when an image of a white subject is picked up by using a light source of white light.

The respective color sensitivity characteristics of R, G and B are shown on the right of the respective image data as simplified graphs. The color sensitivity characteristics of R, G and B at this time are respectively set as n-dimensional column vectors "R", "G" and "B".

Next, the electronic endoscope apparatus converts the characteristics of narrow band bandpass filters F1, F2 and F3 as basic spectral characteristics of spectral signals desired to be extracted, for example, three spectral signals (the electronic endoscope apparatus knows the characteristics of the filters which can efficiently extract a structure as anticipation information. The characteristics of the filters respectively have passbands of wavelength bands of substantially 590 nm to substantially 610 nm, substantially 530 nm to substantially 550 nm, and substantially 400 nm to substantially 430 nm) into numeric data.

Here, "substantially" is a concept including about 10 nm in a wavelength. The characteristics of the filters at this time are set as n-dimensional column vectors "F1", "F2" and "F3", respectively. An optimal coefficient set that is approximate to the following relation is found based on the obtained numeric data.

Specifically, the elements of the matrix which satisfies the following Formula 1 is found.

[Formula 1]
$$(R\ G\ B)\begin{pmatrix} a_1 & a_2 & a_3 \\ b_1 & b_2 & b_3 \\ c_1 & c_2 & c_3 \end{pmatrix} = (F_1\ F_2\ F_3) \quad (1)$$

The solution of the above proposition of optimization is mathematically given as follows. When a matrix expressing color sensitivity characteristics of R, G and B is set as "C", a matrix expressing a spectral characteristic of a narrow band bandpass filter desired to be extracted is set as "F", and a coefficient matrix to be found where principal component analysis or orthogonal expansion (or orthogonal transformation) is executed is set as "A",

[Formula 2]

$$C = (R\ G\ B)\quad A = \begin{pmatrix} a_1 & a_2 & a_3 \\ b_1 & b_2 & b_3 \\ c_1 & c_2 & c_3 \end{pmatrix}\quad F = (F_1\ F_2\ F_3) \quad (2)$$

is established. Accordingly, the proposition shown in the Formula (1) is equal to finding the matrix "A" which satisfies the following relationship.

[Formula 3]

$$CA = F \quad (3)$$

Here, as a number n of point sequences as spectral data expressing a spectral characteristic, n>3 is set, therefore, the Formula (3) is not a one-dimensional simultaneous equation, but is given as a solution of a linear minimum square method. Specifically, a quasi-inverse matrix is solved from the Formula (3). When a transposed matrix of the matrix "C" is set as "$^tC$", Formula (3) becomes [Formula 4].

$$^tCCA = ^tCF \quad (4)$$

Since "$^tCC$" is a square matrix of n×n, the Formula (4) can be considered as a simultaneous equation about the matrix "A", and its solution is given by [Formula 5]

$$A = (^tCC)^{-1}\,^tCF \quad (5)$$

By performing conversion of the left side of the Formula (3) about the matrix "A" found by the Formula (5), the electronic endoscope apparatus can obtain approximation of the characteristics of the narrow band bandpass filters F1, F2 and F3 desired to be extracted. The above is the description of the matrix calculation method that is the basis of the present invention.

By using the matrix thus calculated, the matrix computing section 436 which will be described later creates a spectral image signal from an ordinary color image signal.

(Correction Method)

Next, a correction method for finding a more accurate spectral image signal will be described.

In the above described explanation of the matrix calculating method, the matrix calculating method is accurately applied when a luminous flux received by a solid state image pickup device such as a CCD is completely white light (all the wavelength intensities are the same in a visible range). Specifically, when the outputs of R, G and B are all the same, optimal approximation is obtained.

However, under actual endoscope observation, the luminous flux for illumination (luminous flux of a light source) is not completely white light, and reflection spectral of a living body is not uniform. Therefore, the luminous flux received by the solid state image pickup element is not white light (since it is colored, the values of R, G and B are not the same).

Accordingly, in order to solve the proposition shown in the Formula (3) more accurately in the actual processing, it is desirable to consider the spectral characteristics of illumination light as spectral sensitivity characteristics of an illumination section, and the reflection characteristics of a living body as the collection of the spectral characteristic data of a test subject, in addition to the color sensitivity characteristics of R, G and B as the spectral sensitivity characteristics of the image pickup unit.

Here, the color sensitivity characteristics (spectral sensitivity characteristics of the image pickup unit) are set as R(λ), G(λ) and B(λ), one example of the spectral characteristics of illumination light (spectral sensitivity characteristics of the illumination section) is set as S(λ), and one example of the reflection characteristics of a living body (collection of the spectral characteristic data of the test subject) is set as H(λ). The spectral characteristics of the illumination light and the reflection characteristics of the living body do not always have to be the characteristics of the apparatus and the subject with which examination is performed, but may be general characteristics which are acquired in advance, for example.

By using these coefficients, correction coefficients $k_R$, $k_G$ and $k_B$ are given by [Formula 6]

$$k_R = (\int S(\lambda) \times H(\lambda) \times R(\lambda) d\lambda)^{-1}$$

$$k_G = (\int S(\lambda) \times H(\lambda) \times G(\lambda) d\lambda)^{-1}$$

$$k_B = (\int S(\lambda) \times H(\lambda) \times B(\lambda) d\lambda)^{-1} \quad (6)$$

When the sensitivity correction matrix is set as "K", "K" is given as follows.

[Formula 7]

$$K = \begin{pmatrix} k_R & 0 & 0 \\ 0 & k_G & 0 \\ 0 & 0 & k_B \end{pmatrix} \quad (7)$$

Accordingly, the coefficient matrix "A" is as follows by adding correction of the Formula (7) to the Formula (5).

[Formula 8]

$$A^t = KA = K(^tCC)^{-1}\,^tCF \quad (8)$$

When optimization is actually performed, allowing a part of the optimized sensitivity distribution to be negative is added by using the fact that when the spectral sensitivity characteristics of the target filters (F1, F2, and F3 in FIG. 1: basic spectral characteristics) are negative, they becomes zero on the image display (specifically, only the portions having positive sensitivities among the spectral sensitivity characteristics of the filters are used). In order to create narrow band spectral sensitivity characteristics from broad spectral sensitivity characteristics, the electronic endoscope apparatus can create the components approximate to bands having sensitivity by adding negative sensitivity characteristics to the target characteristics of F1, F2 and F3 as shown in FIG. 1.

(Method for Improving S/N)

Next, a method for improving S/N and precision of the created spectral image signal will be described. The method for improving the S/N ratio further solves the following problem by being added to the above described processing method.

(i) If any of the original signals (R, G and B) in the above described matrix calculation method is saturated, the characteristics of the filters F1 to F3 in the processing method are likely to differ greatly from the characteristics of the filters which can efficiently extract the structure (ideal characteristics) (when the filters F1 to F3 are created by two signals out of R, C and B, both the two original signals need to be unsaturated).

(ii) At the time of conversion from a color image signal to a spectral image signal, a narrow band filter is created from a wide band filter. Therefore, degradation of sensitivity occurs, the component of the created spectral image signal becomes small, and the S/N ratio is not favorable.

In the method for improving an S/N ratio, irradiation of illumination light is separately performed several times (for example, n times, n is an integer of 2 or more) in one filed (one frame) of an ordinary image (an ordinary color image) (Irradiation intensity may be changed each time. In FIG. 2, irradiation intensities are expressed by I0 to In. This can be realized by only control of the illumination light.) as shown in FIG. 2.

Thereby, the electronic endoscope apparatus can make irradiation intensity of one time small, and can restrain the R, G and B signals from being saturated respectively. The separated image signals at several times are added by the amount of n in a post stage. Thereby, the electronic endoscope apparatus makes the signal component large, and can improve the S/N ratio. In FIG. 2, the integrating sections 438*a* to 438*c* function as image quality adjusting sections which improve the S/N ratio.

The above is the explanation of the matrix computing method which is the basis of the present invention, the correction method for finding an accurate spectral image signal which can be carried out with the matrix computing method, and the method for improving the S/N ratio of the created spectral image signal.

Here, a modified example of the above described matrix calculating method will be described.

MODIFIED EXAMPLE OF MATRIX CALCULATING METHOD

The color image signals (spectral sensitivity characteristics of the image pickup unit) are set as R, G and B, and the estimated spectral image signals (basic spectral characteristics) are set as F1, F2 and F3. More strictly, the color image signals R, G and B are the functions of positions x and y on an image, and therefore, they should be expressed as, for example, R (x,y), but such expression will be omitted here.

It is a target to estimate the matrix "A" of three by three for calculating F1, F2 and F3 from R, G and B. If "A" is estimated, calculation of F1, F2 and F3 from R G and B becomes possible from the following Formula (9).

[Formula 9]

$$\begin{pmatrix} F_1 \\ F_2 \\ F_3 \end{pmatrix} = A \begin{pmatrix} R \\ G \\ B \end{pmatrix} \tag{9}$$

Here, expression of the following data will be defined.

The spectral characteristics of a test subject: $H(\lambda)$, "H"= $(H(\lambda 2), H(\lambda 2), \ldots, H(\lambda n))^t$ where $\lambda$ denotes a wavelength, and t denotes transposition in matrix computation. Likewise, the spectral characteristics of illumination light: $S(\lambda)$, "S"= $(S(\lambda 2), S(\lambda 2), \ldots, S(\lambda n))^t$ The spectral sensitivity characteristics of a CCD; $J(\lambda)$, "J"= $(J(\lambda 2) J(\lambda 2), \ldots, J(\lambda n))^t$ The spectral characteristics of the filters which perform color separation: in the case of primary colors $R(\lambda)$, "R"=$(R(\lambda 2), R(\lambda 2), \ldots, R(\lambda n))^t$ $G(\lambda)$, "G"=$(G(\lambda 2), G(\lambda 2), \ldots, G(\lambda n))^t$ $B(\lambda)$, "B"=$(B(\lambda 2), B(\lambda 2), \ldots, B(\lambda n))^t$ "R", "G" and "B" are organized into one by the matrix "C" as shown in Formula (10).

[Formula 10]

$$C = \begin{pmatrix} R \\ G \\ B \end{pmatrix} \tag{10}$$

The image signals R, G and B, and the spectral signals F1, F2 and F3 are expressed by the matrixes as follows.

[Formula 11]

$$P = \begin{pmatrix} R \\ G \\ B \end{pmatrix}, Q = \begin{pmatrix} F_1 \\ F_2 \\ F_3 \end{pmatrix} \tag{11}$$

The image signal "P" is calculated by the following formula.
[Formula 12]

$$P = CSJH \tag{12}$$

When the color separation filter for obtaining "Q" is set as "F", similarly to Formula (12),
[Formula 13]

$$Q = FSJH \tag{13}$$

Here, if it is assumed that the spectral reflectance of a test subject can be expressed by approximation with the linear sum of a plurality of basic (three in this case) spectral characteristics as an important first assumption, "H" can be expressed as follows.
[Formula 14]

$$H \approx DW \tag{14}$$

Here, "D" denotes a matrix having three basic spectrums $D1(\lambda)$, $D2(\lambda)$ and $D3(\lambda)$ as column vectors, "W" denotes a weighting factor expressing contribution of $D1(\lambda)$, $D2(\lambda)$ and $D3(\lambda)$ to "H". When the color tone of the test subject does not vary so much, the approximation is known to be established.

When the Formula (14) is substituted into the Formula (12), the following formula is obtained.
[Formula 15]

$$P = CSJH = CSJDW = MW \tag{15}$$

Here, a matrix "M" of 3 by 3 represents the matrix in which the calculation results of matrixes "CSJD" are organized into one.

Likewise, the Formula (14) is substituted into the Formula (13), and the following formula is obtained.
[Formula 16]

$$Q = FSJH = FSJDW = M'W \tag{16}$$

Similarly, "M'" represents the matrix in which the calculation results of matrixes "FSJD" are organized into one.

Ultimately, "W" is eliminated from the Formula (15) and Formula (16), and the following formula is obtained.
[Formula 17]

$$Q = M'M^{-1}P \tag{17}$$

"$M^{-1}$" represents an inverse matrix of the matrix "M". Ultimately, "$M'M^{-1}$" becomes a matrix of 3 by 3, and the matrix "A" of the estimation target.

Here, it is assumed that when color separation is performed with a bandpass filter, the spectral characteristic of the test subject in the band can be approximated with one numeric value, as an important second assumption. Specifically, [Formula 18]

$$H=(h_1, h_2, h_3)^t \quad (18)$$

Considering the case in which the bandpass for color separation is not a complete bandpass, but has sensitivity in other bands, when the assumption is established, if each "W" in the Formula (15) and Formula (16) is considered as the above described "H", the same matrix as the Formula (17) can be ultimately estimated.

Next, a concrete configuration of the electronic endoscope apparatus as a biological observation apparatus according to the embodiment one of the present invention will be described with reference to FIG. 3. Other embodiments which will be described later have similar configurations.

As shown in FIG. 3, an electronic endoscope apparatus 100 as a biological observation apparatus has an endoscope 101 as an observation unit, an endoscope apparatus main body 105, and a display monitor 106 as a display device or a display output device. The endoscope 101 is mainly configured by an insertion portion 102 which is inserted into a body cavity of a test subject a distal end portion 103 provided at a distal end of the insertion portion 102, and an angle operation portion 104 which is provided at an opposite side from a distal end side of the insertion portion 102 to instruct a bending operation or the like of the distal end portion 103.

An image of the test subject obtained with the endoscope 101 which is a flexible endoscope is subjected to predetermined signal processing in the endoscope apparatus main body 105, and the processed image is displayed in the display monitor 106.

Next, the endoscope apparatus main body 105 will be described in detail with reference to FIG. 4. FIG. 4 is a block diagram of the electronic endoscope apparatus 100.

As shown in FIG. 4, the endoscope apparatus main body 105 is mainly configured by a light source unit 41 as an illumination unit, a control unit 42 and a main body processing device 43. The control unit 42 and the main body processing device 43 configure a signal processing control unit which controls the operation of a CDD 21 as the light source unit 41 and/or an image pickup unit, and outputs an image pickup signal to the display monitor 106 that is a display device.

In the present embodiment, explanation will be made on the precondition that the light source unit 41 and the main body processing device 43 which performs image processing and the like are included in the endoscope apparatus main body 105 which is one unit, but the light source unit 41 and the main body processing device 43 may be configured to be detachable as a separate unit from the endoscope apparatus main body 105.

The light source unit 41 which is an illumination unit is connected to the control unit 42 and the endoscope 101, and performs irradiation of white light (including the case of incomplete white light) with a predetermined light quantity based on a signal from the control unit 42. The light source unit 41 has a lamp 15 as a white light source, a chopper 16 for adjusting a light amount, and a chopper drive section 17 for driving the chopper 16.

The chopper 16 includes a configuration in which notch portions having predetermined lengths in a circumferential direction are provided at a disk-shaped structure with a point 17a as a center and a predetermined radius r0, as shown in FIG. 5. The center point 17a is connected to a rotary shaft provided at the chopper drive section 17. Specifically, the chopper 16 performs rotational movement around the center point 17a. A plurality of notch portions are provided at predetermined radiuses. In FIG. 5, the notch portion has the maximum length=2πr0×2θ0 degrees/360 degrees, and width=r0–ra between the radius r0 and a radius ra. Similarly, the notch portion has the maximum length=2πra×2θ1 degrees/360 degrees and width=ra–rb between the radius ra and a radius rb, and the notch portion has the maximum length=2πrb×2θ2 degrees/360 degrees and width=rb–rc between the radius rb and a radius rc (the respective radiuses satisfy r0>ra>rb>rc).

The length and width of each of the notch portions in the chopper 16 are only examples, and are not limited to the present embodiment.

The chopper 16 has a projection portion 160a extending in the radius direction in a substantially center of the notch portions. The control unit 42 minimizes an interval of lights irradiated one frame before and one frame later by switching the frame when the light is shielded by the projection portion 160a, and minimizes blurring due to motion or the like of the test subject.

The chopper drive section 17 is configured to be movable in a direction toward the lamp 15 as shown by the arrows in FIG. 4.

Specifically, the control unit 42 can change a distance R between the rotational center 17a of the chopper 16 and a luminous flux (shown by a dotted line circle) from the lamp shown in FIG. 5. For example, in the state shown in FIG. 5, the distance R is considerably small, and therefore, the illumination light quantity is in a small state. By making the distance R large (moving the chopper drive section 17 away from the lamp 15), the notch portion in which the luminous flux can pass becomes long. Therefore, the irradiation time becomes long, and the control unit 42 can make the illumination light quantity large.

As described above, in the electronic endoscope apparatus, a newly created spectral image is likely to be insufficient as S/N, and when any signal out of the R, G and B signals necessary for creation of the spectral image is saturated, correct computation is not performed. Therefore, illumination light quantity needs to be controlled. The chopper 16 and the chopper drive section 17 bear adjustment of the light quantity.

The endoscope 101 connected to the light source unit 41 via a connector 11 includes an objective lens 19 and a solid state image pickup device 21 such as a CCD (hereinafter, simply described as the CCD) at the distal end portion 103. The CCD in the present embodiment is of a single-panel type (CCD used for a simultaneous type electronic endoscope), and of a primary color type. FIG. 6 shows arrangement of color filters disposed on an image pickup surface of the CCD. The color filters disposed on the image pickup surface of the CCD configure a color separating portion. FIG. 7 shows the respective spectral sensitivity characteristics of R, G and B in the color filters of FIG. 6.

As shown in FIG. 4, the insertion portion 102 includes a light guide 14 which guides the light irradiated from the light source unit 41 to the distal end portion 103, a signal line for transferring an image of the test subject obtained with the CCD to the main body processing device 43, a forceps channel 28 for performing treatment and the like. A forceps port 29 for inserting forceps into the forceps channel 28 is provided near the operation portion 104.

The main body processing device 43 as a signal processing device for the biological observation apparatus is connected to the endoscope 101 via the connector 11 similarly to the light source unit 41. The main body processing device 43 includes a CCD drive 431 for driving the CCD 21. The main body processing device 43 has a luminance signal processing system and a color signal processing system as signal circuit systems for obtaining an ordinary image.

The luminance signal processing system has a contour correcting section 432 which is connected to the CCD 21 to perform contour correction, and a luminance signal processing section 434 which creates a luminance signal from data corrected in the contour correcting section 432. The color signal processing system has sample hold circuits (S/H circuits) 433a to 433c which are connected to the CCD 21, and perform sampling of signals obtained in the CCD 21 to create R, G and B signals, and a color signal processing section 435 which is connected to the outputs of the S/H circuits 433a to 433c to perform creation of color signals.

An ordinary image creating section 437 which creates one ordinary image from the output of the luminance signal processing system and the output of the color signal processing system is provided, and a Y signal, an R-Y signal and a B-Y signal are sent to the display monitor 106 via a switching section 439 from the ordinary image creating section 437.

Meanwhile, as a signal circuit system for obtaining a spectral image, a matrix computing section 436 which has the outputs (RGB signals) of the S/H circuits 433a to 433c inputted therein and performs predetermined matrix computation for the R, G and B signals is provided. The matrix computing section 436 configures a spectral signal creating section. Matrix computation means the processing of performing addition processing or the like for the color image signals, and multiplying them by the matrix found by the above described matrix calculating method (or its modified example).

In the present embodiment, as the method for the matrix computation, a method using electronic circuit processing (processing by hardware using an electronic circuit) will be described, but a method using numeric data processing (processing by software using a program) as in an embodiment which will be described later may be adopted. In carrying out matrix computation, these methods can be combined.

FIG. 8 shows a circuit diagram of the matrix computing section 436. The R, G and B signals are inputted into amplifiers 32a to 32c via resistance groups 31a to 31c. The respective resistance groups have a plurality of resistances to which the R, G and B signals are respectively connected, and the resistance values of the respective resistances are the values corresponding to the matrix coefficients. Specifically, the matrix computing section 436 has a configuration in which the amplification factors of the R, G and B signals are changed by the respective resistances, and added (may be subtracted) with the amplifiers. The outputs of the respective amplifiers 32a to 32c become the outputs of the matrix computing section 436. Specifically, the matrix computing section 436 performs so-called weighting addition processing. The resistance values in the respective resistances used here may be made variable.

The outputs of the matrix computing section 436 are respectively connected to integrating sections 438a to 438c. After integrating computation is performed there, color adjusting computation which will be described later is performed for respective spectral image signals ΣF1 to ΣF3 in a color adjusting section 440, and spectral color channel image signals R(ch), G(ch) and B(ch) are created from the spectral image signals ΣF1 to ΣF3. The created spectral color channel image signals Rch, Gch and Bch are sent to color channels R(ch), G(ch) and B(ch) of R, G and B of the display monitor 106 via the switching section 439. A configuration of the color adjusting section 440 will be described later.

The switching section 439 performs switching of an ordinary image and a spectral image, and can perform switching between spectral images for display. Specifically, an operator can cause the display monitor 106 to display an image selectively from an ordinary image, a spectral color channel image by the color channel R(ch), a spectral color channel image by the color channel G(ch) and a spectral color channel image by the color channel B(ch). A configuration in which any two or more images can be simultaneously displayed in the display monitor 106 may be adopted. Especially when an ordinary image and a spectral color channel image (hereinafter, also called a spectral channel image) are made simultaneously displayable, the ordinary image ordinarily performing observation can be easily contrasted with the spectral channel image, and observation can be made by incorporating the respective characteristics (The characteristic of the ordinary image is that the ordinary image has the chromaticity close to ordinary observation by naked-eyes and easy to observe. The characteristic of the spectral channel image is that a predetermined vessel or the like which cannot be observed in an ordinary image can be observed.), which is very useful in diagnosis.

Figure 35:
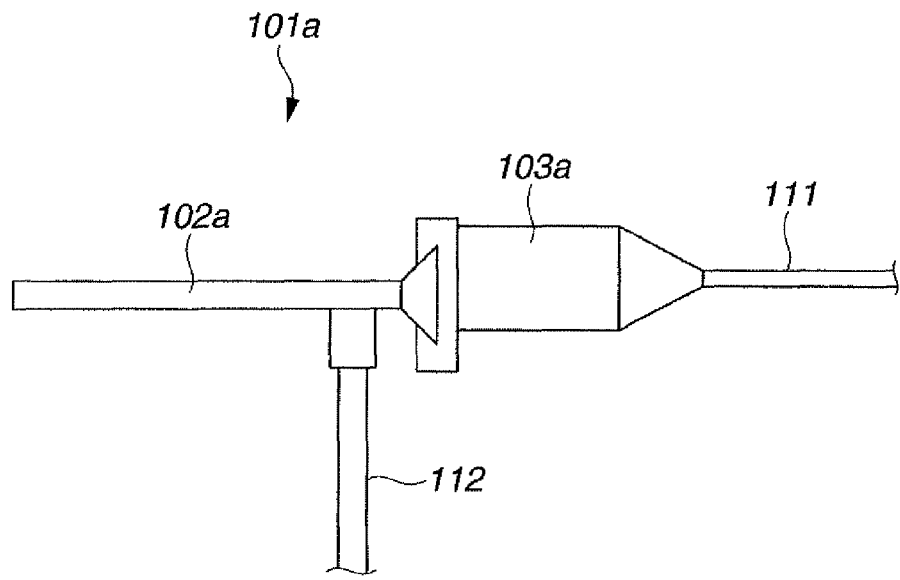
FIG. 35 is a view showing an appearance of a rigid endoscope.

The scope 101 that is an endoscope configured as a flexible endoscope used in the present embodiment may be an endoscope configured as a rigid endoscope such as an endoscope 101a shown in FIG. 35, for example.

The endoscope 101a has a rigid insertion portion 102a which is inserted into a body of a test subject, and a television camera 103a configured to be attachable and detachable to and from a proximal end portion of the insertion portion 102a.

The insertion portion 102a has a cable 112 having a configuration attachable and detachable to and from the light source unit 41 of the endoscope apparatus main body 105. Light guides not shown which guide illumination light from the light source unit 41 to a distal end portion of the insertion portion 102a are provided inside the insertion portion 102a and the cable 112.

Further, the distal end portion of the insertion portion 102a has an objective optical system not shown for forming an image of a test subject. The insertion portion 102a is provided at a proximal end side of the objective optical system and has a relay lens (not shown) at a region from the distal end portion to the proximal end portion.

Since the insertion portion 102a has the above described configuration, the image of the test subject is formed on a distal end surface of the relay lens by the objective optical system, and thereafter, the image is transferred via the relay lens group. Light of the transferred image of the test subject is focused in a CCD (not shown) of the television camera 103a provided at a rear end surface side of the relay lens group. The CCD outputs the focused image of the test subject as an image pickup signal.

The television camera 103a has a cable 111 having a configuration attachable and detachable to and from the main body processing device 43 of the endoscope apparatus main body 105. By such a configuration, the television camera 103a outputs an image pickup signal to the main body processing device 43 via the cable 111.

Figure 36:
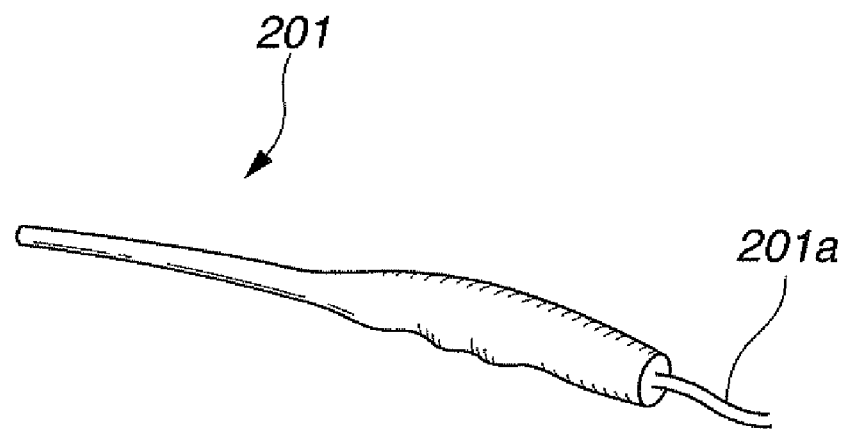
FIG. 36 is a view showing an appearance of an oral camera.

The endoscope 101 used in the present embodiment may be the one configured as an oral camera such as scope 201 shown in FIG. 36, for example.

The scope 201 has at a distal end portion a light source such as an LED not shown which emits illumination light substantially similar to the light source unit 41, an objective optical system not shown which forms an image of a test subject illuminated by the light source, a CCD not shown which is provided at an image forming position of the objective optical system and outputs a picked up image of the test subject as an image pickup signal, and a color filter not shown provided at the CCD, and has at a proximal end portion a cable 201*a* having a configuration attachable and detachable to and from the main body processing device 43.

Figure 37:
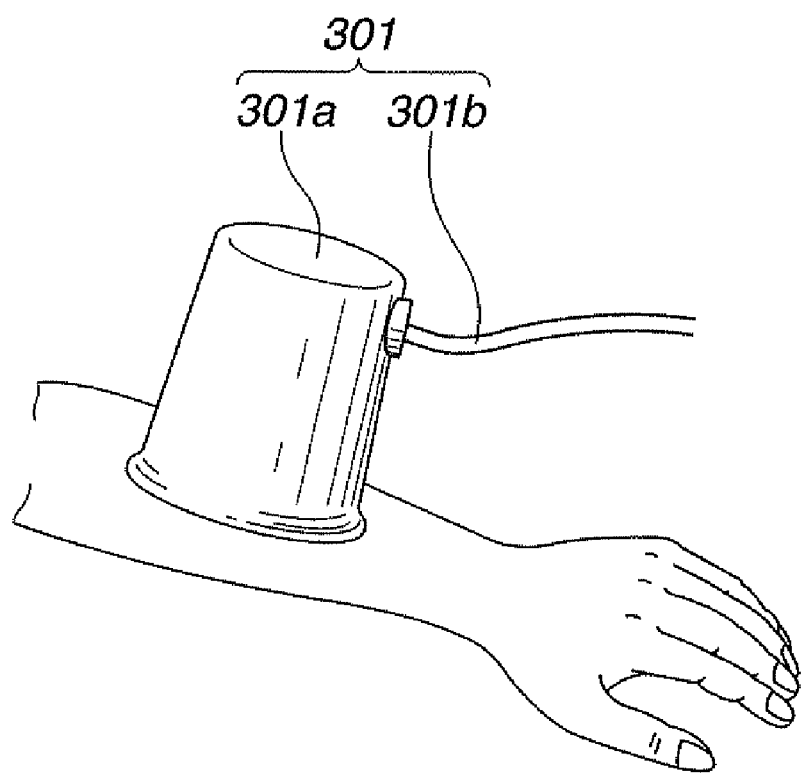
FIG. 37 is a view showing an appearance of a camera used in contact with a living body surface.

The endoscope 101 used in the present embodiment may be the one configured as a camera which is used by being brought into contact with a living body surface such as a scope 301 shown in FIG. 37.

The scope 301 has a contact portion 301*a* provided with a light source such as an LED not shown which emits illumination light and is substantially similar to the light source unit 41, an objective optical system not shown which forms an image of a test subject illuminated by the light source, a CCD not shown which is provided at an image forming position of the objective optical system and outputs a picked-up image of the test subject as an image pickup signal, and a color filter not shown provided at the CCD, and a cable 301*b* which has a configuration attachable and detachable to and from the main body processing device 43, and transfers the image pickup signal from the contact portion 301*a* to the main body processing device 43.

Next, an operation of the electronic endoscope apparatus 100 in the present embodiment will be described in detail with reference to FIG. 4.

Hereinafter, an operation when observing an ordinary image will be described first, and thereafter, an operation when observing a spectral image will be described.

First, an operation of the light source unit 41 will be described. Based on the control signal from the control unit 42, the chopper drive section 17 is set at a predetermined position and rotates the chopper 16. The luminous flux from the lamp 15 passes through the notch portion of the chopper 16, is gathered on an incidence end of the light guide 14 which is an optical fiber bundle provided in the connector 11 that is a connecting portion of the endoscope 101 and the light source unit 41 by a condenser lens.

The gathered luminous flux passes through the light guide 14 and is irradiated into the body of a test subject from the illumination optical system provided at the distal end portion 103. The irradiated luminous flux reflects in the body of the test subject, and signals are collected according to the color filters shown in FIG. 6 in the CCD 21 via the objective lens 19.

The collected signals are inputted in parallel into the above described luminance signal processing system and color signal processing system. In the contour correcting section 432 of the luminance signal system, the signals collected in accordance with the color filters are added and inputted for each pixel, and after contour correction, they are inputted into the luminance signal processing section 434. In the luminance signal processing section 434, a luminance signal is created, and is inputted into the ordinary image creating section 437.

Meanwhile, the signals collected in the CCD 21 are inputted into the S/H circuits 433*a* to 433*b* in accordance with the color filters, and R, G and B signals are created respectively. Further, from the R, G and B signals, color signals are created in the color signal processing section 435, then in the ordinary image creating section 437, a Y signal, an R-Y signal and a B-Y signal are created from the luminance signal and the color signals, and an ordinary image of the test subject is displayed on the display monitor 106 via the switching section 439.

Next, the operation when observing a spectral image will be described. The components which perform the same operations as in the observation of the ordinary image will be omitted here.

An operator performs an instruction for observing a spectral image from an ordinary image, by operating a keyboard provided at the endoscope apparatus main body 105 or a switch or the like provided at the operation portion 104 of the endoscope 101. At this time, the control unit 42 changes the control states of the light source unit 41 and the main body processing device 43.

More specifically, the control unit 42 changes the light quantity irradiated from the light source unit 41 in accordance with necessity. As described above, saturation of the output from the CCD 21 is not desirable, and therefore, the illumination light quantity is made small at the time of observing a spectral image as compared with the time of observing an ordinary image. The control unit 42 can control the light quantity so that the output signal from the CCD is not saturated, and can change the illumination light quantity in the range in which the output signal is not saturated.

As the change of control to the main body processing device 43 by the control unit 42, a signal outputted from the switching section 439 is switched to the output of the color adjusting section 440 from the output of the ordinary image creating section 437. The outputs of the S/H circuits 433*a* to 433*c* are subjected to amplification and addition processing in the matrix computing section 436, and are outputted to the integrating sections 438*a* to 438*c* in accordance with the respective bands, and are outputted to the color adjusting section 440 after being subjected to the integration processing. Even when the illumination light quantity is made small with the chopper 16, intensity of the signals can be increased as shown in FIG. 2 by storing and integrating the signals in the integrating sections 438*a* to 438*c*, and a spectral image enhanced in S/N can be obtained.

The concrete matrix processing of the matrix computing section 436 in the present embodiment will be described hereinafter. When the bandpass filters (hereinafter, called quasi-bandpass filters) close to the ideal narrow band bandpass filters F1 to F3 shown in FIG. 7 (in this case, the respective transmission wavelength regions are set at F1: 590 nm to 620 nm, F2; 520 nm to 560 mm, and F3: 400 nm to 440 nm) are to be created from the spectral sensitivity characteristics of the R, G and B color filters shown by the solid lines in FIG. 7, the following matrix is optimal from the contents shown in the above described Formula (1) to Formula (5), in the present embodiment.

[Formula 19]

$$A = \begin{pmatrix} 0.625 & -3.907 & -0.05 \\ -3.097 & 0.631 & -1.661 \\ 0.036 & -5.146 & 0.528 \end{pmatrix} \quad (19)$$

Further, when correction is made from the contents shown in the Formula (6) and Formula (7), the following correction coefficients are obtained.

[Formula 20]

$$K = \begin{pmatrix} 1 & 0 & 0 \\ 0 & 1.07 & 0 \\ 0 & 0 & 1.57 \end{pmatrix} \quad (20)$$

The anticipation information that spectrum S(λ) of the light source shown in the Formula (6) is the one shown in FIG.

9, and a reflection spectrum H(λ) of the living body shown in the Formula (7), to which attention is paid is the one shown in FIG. 10 is used.

Accordingly, the processing performed in the matrix computing section 436 is mathematically equivalent to the following matrix computation.

[Formula 21]

$$A^t = KA = \begin{pmatrix} 1 & 0 & 0 \\ 0 & 1.07 & 0 \\ 0 & 0 & 1.57 \end{pmatrix} \begin{pmatrix} 0.625 & -3.907 & -0.05 \\ -3.097 & 0.631 & -1.661 \\ 0.036 & -5.146 & 0.528 \end{pmatrix} \quad (21)$$

$$= \begin{pmatrix} 0.625 & -3.907 & -0.050 \\ -3.314 & 0.675 & -1.777 \\ 0.057 & -8.079 & 0.829 \end{pmatrix}$$

By performing the matrix computation, the quasi-filter characteristics (shown as the filters quasi—F1 to F3 in FIG. 7) are obtained. Specifically, the above described matrix processing creates spectral image signals by using the quasi-bandpass filters (matrix) created in advance as described above for the color image signals.

One example of the endoscope image created by the quasi-filter characteristics will be shown hereinafter.

As shown in FIG. 11, a tissue 45 in a body cavity often has an absorber distribution structure of different blood vessels and the like in a depth direction, for example. Many capillary vessels 46 are mainly distributed near a mucosal surface layer, and blood vessels 47 thicker than the capillary vessels are distributed in an intermediate layer which is deeper than the mucosal surface layer, in addition to the capillary vessels. Thicker blood vessels 48 are further distributed in a deeper layer.

Meanwhile, the depth of invasion of light in the depth direction with respect to the tissue 45 in the body cavity depends on the wavelength of the light, and as for illumination light including a visible region, in the case of light with a short wavelength such as blue (B) light, the light reaches only a region near the surface layer due to the absorption characteristic and scattering characteristic in the biological tissue, the light is subjected to absorption and scattering in the range of the depth up to the surface layer, and the light exiting from the surface is observed as shown in FIG. 12. In the case of green (G) light with a wavelength longer than the blue (B) light, the light reaches to a place deeper than the range which the blue (B) light reaches, and is subjected to absorption and scattering in that range, and the light exiting from the surface is observed. Furthermore, in the case of red (R) light with a longer wavelength than the green (G) light, the light reaches a deeper range.

Since the respective wavelength regions of the R, G and B light at the time of ordinary observation of the tissue 45 in the body cavity overlap one another as shown in FIG. 13, (1) in an image pickup signal picked up with the CCD 21 by B band light, a band image having shallow layer and intermediate layer tissue information including much tissue information in the shallow layer as shown in FIG. 14 is picked up, (2) in an image pickup signal picked up with the CCD 21 by G band light, a band image having shallow layer and intermediate layer tissue information including much tissue information in the intermediate layer as shown in FIG. 15 is picked up, and (3) in an image pickup signal picked up with the CCD 21 by R band light, a band image having intermediate layer and deep layer tissue information including much tissue information in the deep layer as shown in FIG. 16 is picked up.

By performing signal processing for the R, G and B image pickup signals by the endoscope apparatus main body 105, an endoscope image with desired or natural color reproduction as an endoscope image can be obtained.

The matrix processing in the above described matrix computing section 436 creates spectral image signals by using quasi-bandpass filters (matrix) created in advance as described above for the color image signals. By using the quasi-bandpass filters F1 to F3 with the discrete and narrow band spectral characteristics capable of extracting desired deep layer tissue information as shown in FIG. 17, for example, the spectral image signals F1 to F3 are obtained. Since the respective wavelength regions of the quasi-bandpass filters F1 to F3 do not overlap one another as shown in FIG. 17, (4) in the spectral image signal F3 by the quasi-bandpass filter F3, a band image having tissue information in the shallow layer as shown in FIG. 18 is picked up, (5) in the spectral image signal F2 by the quasi-bandpass filter F2, a band image having tissue information in the intermediate layer as shown in FIG. 19 is picked up, and (6) in the spectral image signal F1 by the quasi-bandpass filter F1, a band image having tissue information in the deep layer as shown in FIG. 20 is picked up.

Next, for the spectral image signals F1 to F3 thus obtained, the color adjusting section 440 assigns the spectral image signal F1 to the color channel R(ch), the spectral image signal F2 to the color channel G(ch), and the spectral image signal F3 to the color channel B(ch) respectively as an example of the simplest color conversion, and outputs them to the display monitor 106 via the switching section 439.

The color adjusting section 440 is configured by a color conversion processing circuit 440a including a three by three matrix circuit 61, three sets of LUTs 62a, 62b, 62c, 63a, 63b and 63c provided before and behind the three by three matrix circuit 61, and a coefficient changing circuit 64 which changes table data of the LUTs 62a, 62b, 62c, 63a, 63b and 63c and the coefficients of the three by three matrix circuit 61, as shown in FIG. 21.

For the spectral image signals F1 to F3 which are inputted into the color conversion processing circuit 440a, inverse γ correction, nonlinear contrast conversion processing and the like are performed for each band data by the LUTs 62a, 62b and 62c.

Next, after color conversion is performed in the three by three matrix circuit 61, γ correction and proper tone transformation processing are performed in the LUTs 63a, 63b and 63c at the post stage.

The table data of the LUTs 62a, 62b, 62c, 63a, 63b and 63c and the coefficients of the three by three matrix circuit 61 can be changed by the coefficient changing circuit 64.

Change by the coefficient changing circuit 64 is performed based on the control signal from the processing conversion switch (not shown) provided at the operation portion or the like of the endoscope 101.

The coefficient changing circuit 64 which receives these control signals calls suitable data from the coefficient data written in the color adjusting section 440 in advance, and rewrites the present circuit coefficients with the data.

Next, a concrete color conversion processing content will be described. Formula (22) shows one example of a color conversion formula.

[Formula 22]

$$\begin{pmatrix} R_{ch} \\ G_{ch} \\ B_{ch} \end{pmatrix} = \begin{pmatrix} 1 & 0 & 0 \\ 0 & 1 & 0 \\ 0 & 0 & 1 \end{pmatrix} \begin{pmatrix} F_1 \\ F_2 \\ F_3 \end{pmatrix} \quad (22)$$

The processing by Formula (22) is color conversion in which the spectral image signals F1 to F3 are assigned to the spectral channel image signals Rch, Gch and Bch in the order of wavelength, the shortest wavelength first.

When observation is made with the color image by the color channels R(ch), G(ch) and B(ch), an image as shown in FIG. 22, for example, is obtained. A thick blood vessel is in a deep position, the spectral image signal F3 is reflected, and the thick blood vessel is shown as a blue pattern as a color image as a predetermined target color. Vascular plexuses near an intermediate layer are shown as a red pattern as a color image as a predetermined target color since the spectral image signal F2 is intensely reflected. Among the vascular plexuses, the ones existing near a mucosal surface are expressed as a yellow pattern as a predetermined target color.

Change in the pattern near the mucosal surface is especially important for discovery and differential diagnosis of early lesion. However, the yellow pattern as the predetermined target color has the tendency to be low in contrast with the background mucosa, and low in visibility.

Thus, in order to reproduce the pattern near the mucosal surface more clearly, conversion shown in Formula (23) becomes effective.

[Formula 23]

$$\begin{pmatrix} R_{ch} \\ G_{ch} \\ B_{ch} \end{pmatrix} = \begin{pmatrix} 1 & 0 & 0 \\ 0 & \omega_G & \omega_B \\ 0 & 0 & 1 \end{pmatrix} \begin{pmatrix} F_1 \\ F_2 \\ F_3 \end{pmatrix} \quad (23)$$

The processing by the Formula (23) is a conversion example in which the data created by mixing the spectral image signal F1 into the spectral image signal F2 at a constant ratio is newly made a spectral G channel image signal Gch as a predetermined target color, and can clarify that the absorbers and scatters such as vascular plexuses differ depending on the depth position.

Accordingly, by adjusting the matrix coefficients through the coefficient changing circuit 64, a user can adjust the display effect. As the operation, the matrix coefficients are set at default values from a through operation in the image processing section by being linked to a mode change-over switch (not shown) provided at the operation portion of the endoscope 101.

The through operation mentioned here means the state in which a unit matrix is loaded on the three by three matrix circuit 61, and non-conversion table is loaded on the LUTs 62a, 62b, 62c, 63a, 63b and 63c. The default value means that set values of, for example, $\omega_G$=0.2, and $\omega_B$=0.8 are given to the matrix coefficients $\omega_G$ and 107 $_B$.

Subsequently, the user operates the operation portion or the like of the endoscope 101, and adjusts the coefficients to $\omega_G$=0.4, $\omega_B$=0.6 and the like. The inverse γ correction table and the γ correction table are applied to the LUTs 62a, 62b, 62c, 63a, 63b and 63c in accordance with necessity.

The color conversion processing circuit 440a performs color conversion by the matrix computer configured by the three by three matrix circuit 61, but the color conversion processing circuit is not limited to this, and the color conversion processing circuit may be configured by a numeric processor (CPU) and a LUT.

For example, in the above described embodiment, the color conversion processing circuit 30a is shown by the configuration with the three by three matrix circuit 61 as the center, but the same effect can be obtained even when the color conversion processing circuit 30a is replaced with the three-dimensional LUTs 65 corresponding to the respective bands as shown in FIG. 23. In this case, the coefficient changing circuit 64 performs an operation of changing the content of the table based on the control signal from the processing converting switch (not shown) provided at the operation portion or the like of the endoscope 101.

The filter characteristics of the quasi-bandpass filters F1 to F3 are not limited to the visible light region, but as a first modified example of the quasi-bandpass filters F1 to F3, the filter characteristics may be in the narrow band with the discrete spectral characteristics as shown in FIG. 24, for example. The filter characteristics of the first modified example are favorable to obtain image information which cannot be obtained in ordinary observation by setting the F3 in a near ultraviolet range and the F1 is set in a near infrared range to observe irregularities on the living body surface and absorbers near the extremely deep layer.

As a second modified example of the quasi-bandpass filters F1 to F3, instead of the quasi-bandpass filter F2, two quasi-bandpass filters F3a and F3b with the filter characteristics close to each other in the short wavelength region may be adopted as shown in FIG. 25. This is suitable for visualizing a subtle difference of scattering characteristics rather than absorption characteristics by using the fact that the wavelength band in the vicinity of this region does not reach the region near the extreme surface layer of a living body. This is assumed to be medically used for discrimination diagnosis of a disease associated with disorder of areolation near a mucosal surface layer such as early cancer.

Further, as a third modified example of the quasi-bandpass filters F1 to F3, the two quasi-bandpass filters F2 and F3 of the narrow band filter characteristics of two bands with discrete spectral characteristics capable of extracting desired layer tissue information as shown in FIG. 26 may be created in the matrix computing section 436.

In the case of the quasi-bandpass filters F2 and F3 of FIG. 26, the color adjusting section 440 creates the spectral channel image signal Rch from the spectral image signal F2, the spectral channel image signal Gch from the spectral image signal F3, and the spectral channel image signal Bch from the spectral image signal F3 in colorization of the image at the time of observation of the spectral image in a narrow band, and creates the color image of three channels of R, G and B.

Specifically, for the spectral image signal F2 and the spectral image signal F3, the color adjusting section 440 creates spectral color channel image signals (Rch, Gch, Bch) of three channels of R, G and B by the following Formula (24).

[Formula 24]

$$\begin{pmatrix} R_{ch} \\ G_{ch} \\ B_{ch} \end{pmatrix} = \begin{pmatrix} h_{11} & h_{12} \\ h_{21} & h_{22} \\ h_{31} & h_{32} \end{pmatrix} \begin{pmatrix} F_2 \\ F_3 \end{pmatrix} \quad (24)$$

For example, h11=1, h12=0, h21=0, h22=1.2, h31=0, h32=0.8

For example, the spectral image F3 of the basic spectral characteristic is an image with the center wavelength mainly corresponding to 415 nm, and the spectral image F2 with the basic spectral characteristic is an image with the center wavelength mainly corresponding to 540 nm.

For example, even when the spectral image F3 of the basic spectral characteristic is computed as an image with the center wavelength mainly corresponding to 415 nm, the spectral image F2 of the basic spectral characteristic is computed as an image with the center wavelength mainly corresponding to 540 nm, and the spectral image F1 with the basic spectral characteristic is computed as an image with the center wavelength mainly corresponding to 600 nm, a color image can be configured by the F2 and F3 images without using the F1 image in the color adjusting section 440. In this case, the matrix computation of the following Formula (24') can be applied instead of the Formula (24).

$Rch = h11 \times F1 + h12 \times F2 + h13 \times F3$ $Gch = h2 \times F1 + h22 \times F2 + h23 \times F3$ $Bch = h31 \times F1 + h32 \times F2 + h33 \times F3$ (24')

In the matrix computation of the above described Formula (24'), the coefficients of h11, h13, h21, h22, h31 and h32 are set at zero, and the other coefficients are set at predetermined numeric values.

Thus, according to the present embodiment, by creating quasi-narrow band filters by using the color image signals for creating an ordinary electronic endoscope image (ordinary image), a spectral image having tissue information at a desired deep portion such as a blood vessel pattern can be obtained without using optical narrow wavelength band bandpass filters for spectral images, and by setting the parameter of the color conversion processing circuit 440a of the color adjusting section 440 in accordance with the spectral image, the expression method which makes the most of the characteristic of depth of invasion information at the time of observation of the spectral image in a narrow band can be realized, so that the tissue information at a desired deep portion near the tissue surface of a biological tissue can be effectively separated and recognized visually.

Thus, the color adjusting section 440 performs signal conversion so that the channel including the test subject information desired to be outputted with the highest contrast among a plurality of spectral signals is reproduced as an image of luminance in the display monitor 106.

Especially in the color adjusting section 440, (1) in the case of a spectral image of two bands, when the image corresponding to, for example, 415 nm is assigned to the color channels G(ch) and B(ch), and the image corresponding to, for example, 540 nm is assigned to the color channel R(ch), or (2) in the case of the spectral image of three bands, when the image corresponding to, for example, 415 nm is assigned to the color channel B(ch), the image corresponding to, for example 445 nm n is assigned to the color channel G(ch), and the image corresponding to, for example, 500 nm is assigned to the color channel R(ch), the following image effects are obtained:

An epithelium or mucosa on the uppermost surface layer of a biological tissue is reproduced in a low chromatic color, and a capillary vessel on the uppermost surface layer is reproduced with low luminance, namely, as a dark line, whereby high visibility of the capillary vessel on the uppermost surface layer is obtained;

At the same time, vessels at the position deeper than capillary vessels are reproduced by being rotated in the blue direction in the hue direction, and therefore, they can be easily discriminated from the capillary vessels on the uppermost surface layer.

According to the method for assigning the channels, in colon fiberscope examination, residue and bile which are observed in a yellow tone under ordinary observation are observed in a red tone.

Embodiment 2

Figure 27:
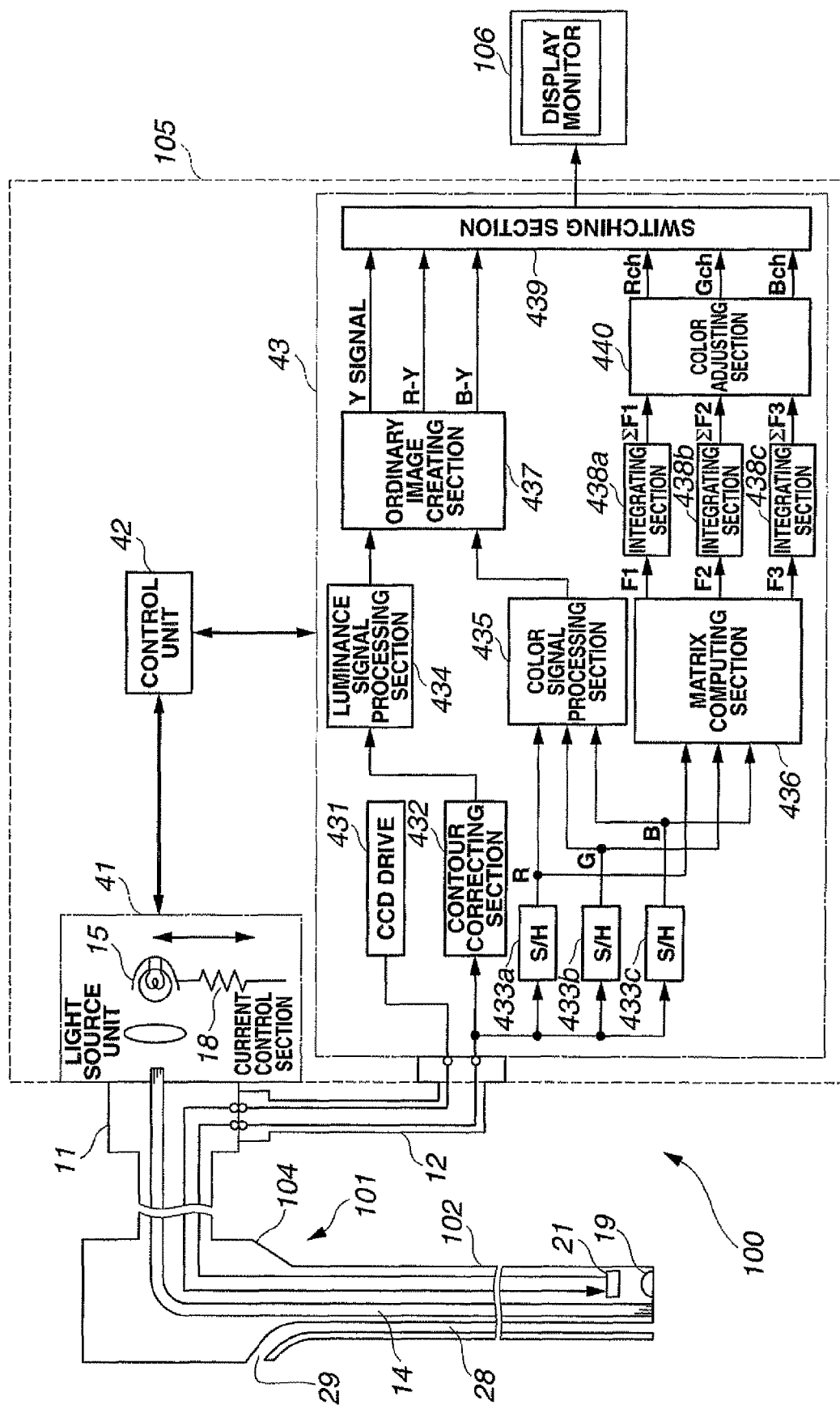
FIG. 27 is a block diagram showing a configuration of an electronic endoscope apparatus according to an embodiment 2 of the present invention.

FIG. 27 is a block diagram showing a configuration of an electronic endoscope apparatus according to an embodiment 2 of the present invention.

Since the embodiment 2 is substantially the same as the embodiment 1, only the different point will be described, and the explanation of the same components will be omitted by being assigned with the same reference numerals and characters as in the first embodiment.

The present embodiment mainly differs from the embodiment 1 in the light source unit 41 which performs control of the illumination light quantity. In the present embodiment, control of the light quantity irradiated from the light source unit 41 is performed by current control of the lamp 15 instead of the chopper. More specifically, a current control section 18 is provided at the lamp 15 shown in FIG. 27.

As an operation of the present embodiment, the control unit 42 controls the current control section 18 and performs control of a current flowing into the lamp 15 so that all the color image signals of R, G and B are not saturated. Thereby, the current used for light emission of the lamp 15 is controlled, and therefore, the light quantity changes in accordance with the magnitude of the current.

Regarding the other operations, they are the same as the embodiment 1, and therefore, the other operations will be omitted.

According to the present embodiment, a spectral image in which a blood vessel pattern is vividly displayed can be obtained as in the embodiment 1. In the present embodiment, the advantage that the control method is simple is obtained as compared with the light quantity control method using the chopper as in the embodiment 1.

Embodiment 3

Figure 28:
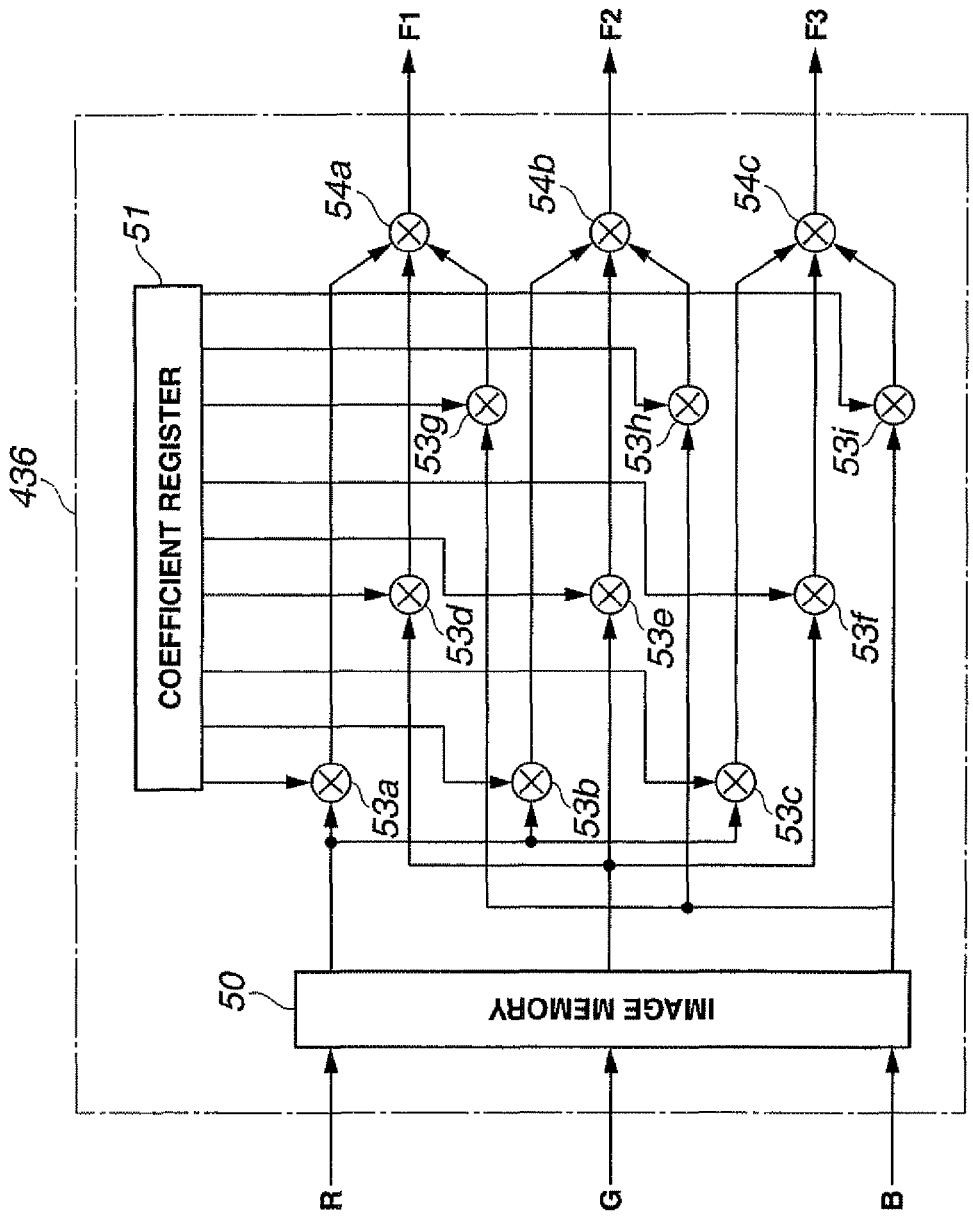
FIG. 28 is a block diagram showing a configuration of a matrix computing section according to an embodiment 3 of the present invention.

FIG. 28 is a block diagram showing a configuration of a matrix computing section according to an embodiment 3.

Since the embodiment 3 is substantially the same as the embodiment 1, only the different point will be described, and the explanation of the same components will be omitted by assigning them with the same reference numerals and characters as the embodiment 1.

The present embodiment differs from the embodiment 1 mainly in the configuration of the matrix computing section 436. In the embodiment 1, the matrix computation is performed by so-called hardware processing by the electronic circuit, but in the present embodiment of FIG. 28, the matrix computation is performed by numeric data processing (processing by software using a program).

A concrete configuration of the matrix computing section 436 in the present embodiment is shown in FIG. 28. The matrix computing section 436 has an image memory 50 which stores respective color image signals of R, G and B. The matrix computing section 436 also has a coefficient register 51 in which the respective values of the matrix "A'" shown in the Formula (21) are stored as numeric data.

The coefficient register 51 and the image memory 50 are connected to multipliers 53*a* to 53*i*, the multipliers 53*a*, 53*d* and 53*g* are further connected to a multiplier 54*a*, and the output of the multiplier 54*a* is connected to the integrating section 438*a* in FIG. 4. The multipliers 53*b*, 53*e* and 53*h* are connected to a multiplier 54*b*, and the output is connected to the integrating section 438*b*. The multipliers 53*c*, 53*f* and 53*i* are connected to a multiplier 54*c*, and the output is connected to the integrating section 438*c*.

As an operation of the present embodiment, the inputted R G B image data are temporarily stored in the image memory 50. Next, by a computation program stored in a predetermined storage device (not shown), each coefficient of the matrix "A'" from the coefficient register 51 is multiplied by the R G B image data stored in the image memory 50 by the multipliers.

FIG. 28 shows an example in which the R signal and each of the matrix coefficients are multiplied in the multipliers 53*a* to 53*c*. As in FIG. 28, the G signal and each of the matrix coefficients are multiplied in the multipliers 53*d* to 53*f*, and the B signal and each of the matrix coefficients are multiplied in the multipliers 53*g* to 53*i*. As for the data multiplied respectively by the matrix coefficients, the outputs of the multipliers 53*a*, 53*d* and 53*g* are multiplied with the multiplier 54*a*, the outputs of the multipliers 53*b*, 53*e* and 53*h* are multiplied with the multiplier 54*b*, and the outputs of the multipliers 53*c*, 53*f* and 53*i* are multiplied with the multiplier 54*c* respectively. The output of the multiplier 54*a* is sent to the integrating section 438*a*. The outputs of the multiplier 54*b* and the multiplier 54*c* are sent to the integrating sections 438*b* and 438*c* respectively.

According to the present embodiment of FIG. 28, the spectral image in which the blood vessel pattern is vividly displayed can be obtained as in the embodiment 1.

In the present embodiment, matrix processing is not performed by the hardware as in the embodiment 1, but is performed by using the software, and therefore, the present embodiment can quickly respond to, for example, change of each of the matrix coefficients or the like.

When only the resultant values of the matrix coefficients are stored, specifically, not as the matrix "A'" but in accordance with S(λ), H(λ), R(λ), G(λ) and B(λ), and the matrix "A'" is found by computation in accordance with necessity and used, only one element among them can be changed, and convenience is enhanced. For example, change of only the spectral characteristic S(λ) of illumination light and the like are possible.

Embodiment 4

Figure 29:
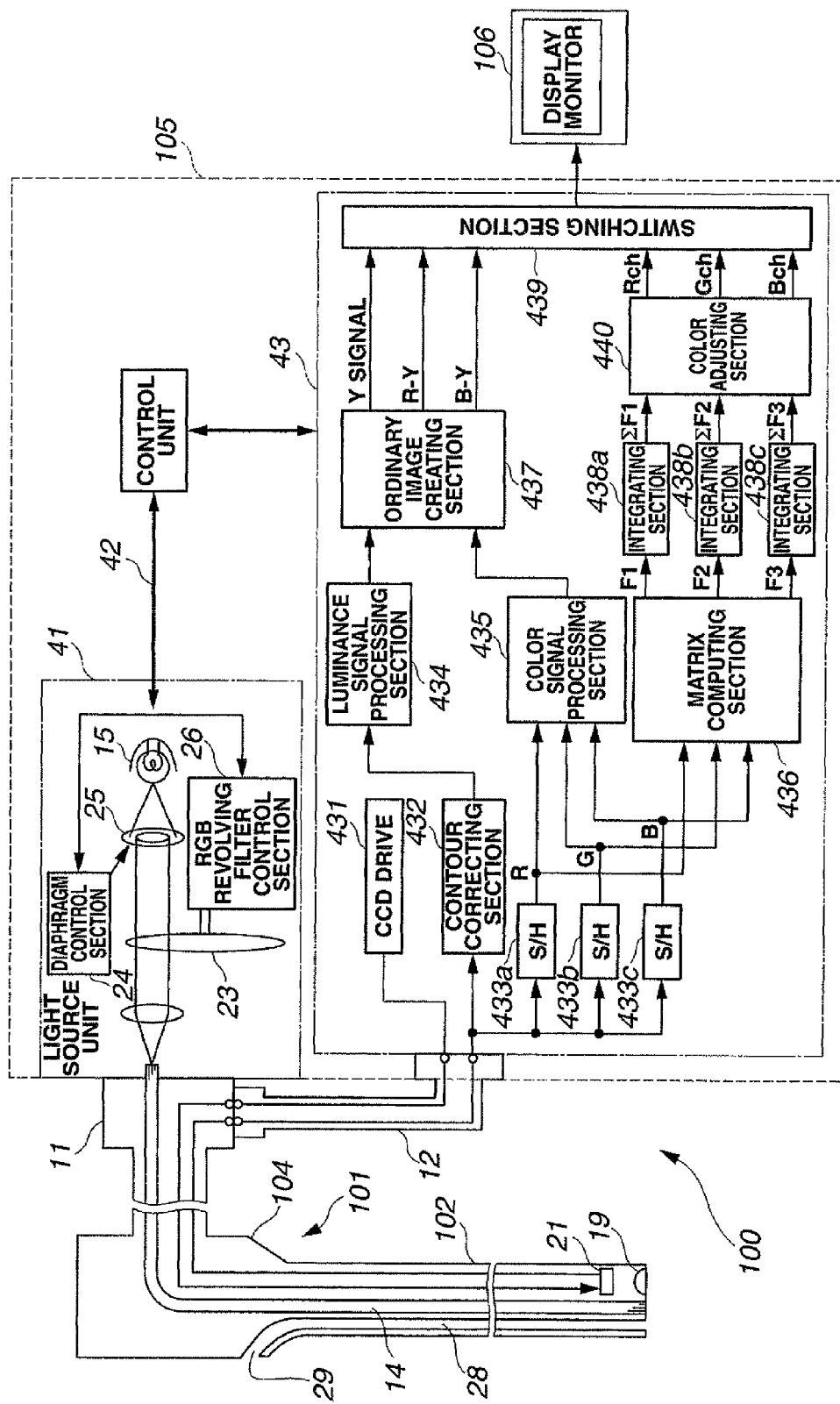
FIG. 29 is a block diagram showing a configuration of an electronic endoscope apparatus according to an embodiment 4 of the present invention.

FIG. 29 and FIG. 30 relate to an embodiment 4 of the present invention, and FIG. 29 is a block diagram showing a configuration of an electronic endoscope apparatus, whereas FIG. 30 is a diagram showing charge storage time of a CCD of FIG. 29.

Since the embodiment 4 is substantially the same as the embodiment 1, only the point differing from the embodiment 1 will be described, and the explanation of the same components will be omitted by assigning them with the same reference numerals and characters as in the embodiment 1.

The present embodiment mainly differs from the embodiment 1 in the light source unit 41 and the CCD 21. In the embodiment 1, a so-called simultaneous method in which color filters shown in FIG. 6 is provided at the CCD 21, and the color signals are created by the color filters is adopted, but in the present embodiment, a so-called frame sequential method in which illumination light is illuminated in the sequence of R, G and G in one frame term to create color signals is used.

As shown in FIG. 29, in the light source unit 41 in the present embodiment, a diaphragm 25 which performs light control is provided at the front surface of the lamp 15, and the RGB filter 23 which makes, for example, one rotation in one frame for emitting frame sequential light of R, G and B is provided further at a front surface of the diaphragm 25. The RGB filter 23 configures a color separating section. The diaphragm 25 is connected to a diaphragm control section 24 as a light quantity control section, and restrains a luminous flux to be transmitted among the luminous fluxes irradiated from the lamp 15 in response to the control signal from the diaphragm control section 24 to change the light quantity, whereby the diaphragm 25 can perform light control. The RGB revolving filter 23 is connected to an RGB revolving filter control section 26 and revolves at a predetermined revolving speed.

As an operation of the light source unit in the present embodiment, the luminous fluxes outputted from the lamp 15 is restrained to have a predetermined light quantity with the diaphragm 25, and the luminous flux which has transmitted through the diaphragm 25 passes through the RGB revolving filter 23, and thereby is outputted from the light source unit as illumination lights of R, G and B at each predetermined time. Each illumination light reflects in the test subject and is received by the CCD 21. The signals obtained by the CCD 21 are distributed by a switching section (not shown) provided in the endoscope apparatus main body 105 in accordance with the irradiated time, and are respectively inputted into the S/H circuits 433*a* to 433*c*. Specifically, when the illumination light through the filter of R is irradiated from the light source unit 41, the signal obtained in the CCD 21 is inputted into the S/H circuit 433*a*. The other operations are the same as the embodiment 1, and therefore, they will be omitted here.

In the present embodiment, the CCD 21 which outputs an image pickup signal based on the image of the reflection light of each illumination light when the test subject is illuminated by each illumination light through the filters of R, G and B is not limited to the one configured as a single-panel type, but may be the one configured as a multiple panel type such as a triple panel type, for example, According to the present embodiment a spectral image in which a blood vessel pattern is vividly displayed can be obtained as in the embodiment 1. In the present embodiment, a merit can be enjoyed by a so-called frame sequential method unlike the embodiment 1. As the merit, the one as in an embodiment 5 which will be described later, for example, can be cited.

In the above described embodiments, in order to avoid saturation of the R, G and B color signals, the illumination light quantity (light quantity from the light source unit) is controlled and adjusted. On the other hand, in the present embodiment, a method for adjusting the electronic shutter of the CCD 21 is adopted. In the CCD 21, the electric charges proportional to the light intensity incident in a constant time accumulate, and the electric charge amount is made a signal. What corresponds to the accumulating time is a so-called electronic shutter. By adjusting the electronic shutter in the CCD drive circuit 431, the accumulation amount of the electric charges, that is, the signal amount can be adjusted. As shown in FIG. 30, by obtaining the R, G and B color images in the state in which the electric charge accumulating time is sequentially changed for each frame, the similar spectral images can be obtained. Specifically, in the above described respective embodiments, control of the illumination light quantity by the diaphragm 25 is used for obtaining an ordinary image, and when the spectral image is obtained, saturation of the R, G and B color signals can be avoided by changing the electronic shutter.

Embodiment 5

FIG. 31 is a diagram showing charge storage time of a CCD according to an embodiment 5 of the present invention.

Since the embodiment 5 is substantially the same as the embodiment 4, only the point differing from the embodiment 4 will be described, and the explanation of the same components will be omitted by assigning them with the same reference numerals and characters as in the embodiment 4.

The present embodiment mainly uses a frame sequential method as the embodiment 4, and makes the most of the advantage of this method. By adding weighting to the charge storage time by the electronic shutter control in the embodiment 4 for each of R, G and B, creation of the spectral image data can be simplified. Specifically, the present embodiment has the CCD drive 431 which can change the charge storage time of the CCD 21 for each of R, G and B within one frame term. The other components are the same as in the embodiment 4.

As an operation of the example of FIG. 31, the charge storage time by the electronic shutter in the CCD 21 is changed when each illumination light is irradiated through the RGB revolving filter 23. Here, the charge storage times of the CCD 21 in the respective cases when the illumination lights are R, G and B are assumed to be tdr, tdg and tdb (in FIG. 31, the color image signal of B is not provided with the storage time, and therefore, tdb is omitted). For example, the F3 quasi-filter image in the case of performing the matrix processing shown by the Formula (21) is obtained by performing the computation of the following Formula (25) from the RGB images ordinarily obtained by the endoscope,

[Formula 25]

$$F3 = -0.050R - 1.777G + 0.829B \quad (25)$$

and therefore, the charge storage times by electronic shutter control according to R, G and B in FIG. 30 can be set so as to satisfy Formula (26).

[Formula 26]

$$tdr:tdg:tdb = 0.050:1.777:0.829 \quad (26)$$

In the matrix computing section, the signals in which an R and G components are simply inversed and a B component are added. Thereby, the similar spectral image to those in the embodiment 1 to embodiment 4 can be obtained.

According to the present embodiment, the spectral image in which blood vessel patterns are vividly displayed can be obtained as in the embodiment 4. In the present embodiment, as in the embodiment 4, a frame sequential method is used for creation of the color signals, and the charge storage time can be made to differ in accordance with the color signals by using the electronic shutter, whereby, in the matrix computing section, addition and subtraction processing only have to be done, and the processing can be simplified.

Embodiment 6

Figure 33:
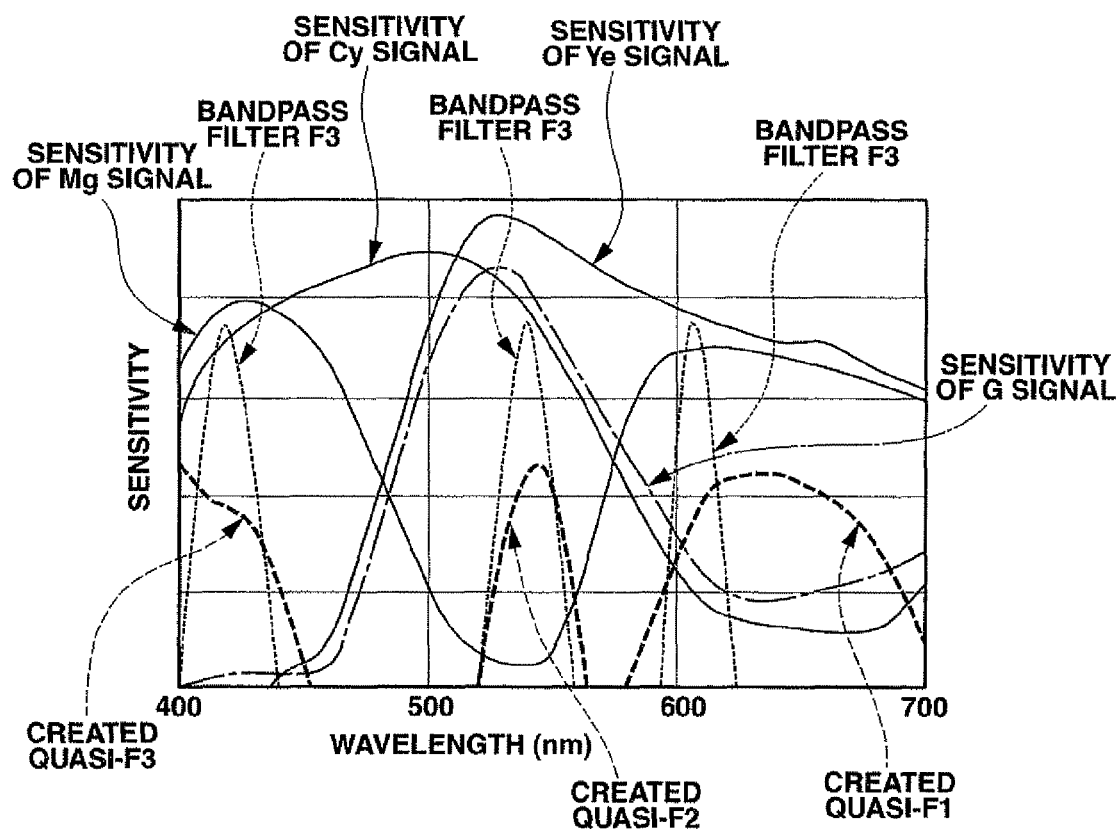
FIG. 33 is a diagram showing spectral sensitivity characteristics of the color filters of FIG. 32.

FIGS. 32 and 33 relate to a biological observation apparatus of an embodiment 6 of the present invention. FIG. 32 is a diagram showing arrangement of color filters. FIG. 33 is a diagram showing spectral sensitivity characteristics of the color filters of FIG. 32.

Since the embodiment 6 is substantially the same as the embodiment 1, only the point differing from the embodiment 1 will be described, and explanation of the same components will be omitted by assigning them with the same numerals and characters as in the embodiment 1.

The present embodiment mainly differs from the embodiment 1 in the color filter provided at the CCD 21. Whereas in the embodiment 1, the RGB primary color type color filter is used as shown in FIG. 6, a complementary color type color filter is used in the present embodiment.

Arrangement of the complementary color type filter is configured by each element of G, Mg, Ye and Cy as shown in FIG. 32. The relationship of each element of the primary color type color filter and each element of the complementary color type color filter is that Mg=R+B, Cy=G+B, and Ye=R+G.

In this case, all the pixels of the CCD 21 are read out, and signal processing or image processing of the image from each of the color filters is performed. When the Formula (1) to Formula (8) and the Formula (19) to Formula (21) about the primary color type color filter are modified for the case of the complementary color type color filter, the following Formula (27) to Formula (33) are obtained. However, the characteristics of the target bandpass filters in a narrow band are assumed to be the same.

[Formula 27]

$$(G \; Mg \; Cy \; Ye) \begin{pmatrix} a_1 & a_2 & a_3 \\ b_1 & b_2 & b_3 \\ c_1 & c_2 & c_3 \\ d_1 & d_2 & d_3 \end{pmatrix} = (F_1 \; F_2 \; F_3) \quad (27)$$

[Formula 28]

$$C = (G \; Mg \; Cy \; Ye) \; A = \begin{pmatrix} a_1 & a_2 & a_3 \\ b_1 & b_2 & b_3 \\ c_1 & c_2 & c_3 \\ d_1 & d_2 & d_3 \end{pmatrix} \; F = (F_1 \; F_2 \; F_3) \quad (28)$$

[Formula 29]

$$k_G = \left( \int S(\lambda) \times H(\lambda) \times G(\lambda) d\lambda \right)^{-1}$$

$$k_{Mg} = \left( \int S(\lambda) \times H(\lambda) \times Mg(\lambda) d\lambda \right)^{-1}$$

$$k_{Cy} = \left( \int S(\lambda) \times H(\lambda) \times Cy(\lambda) d\lambda \right)^{-1}$$

$$k_{Ye} = \left( \int S(\lambda) \times H(\lambda) \times Ye(\lambda) d\lambda \right)^{-1}$$

(29)

[Formula 30]

$$K = \begin{pmatrix} k_G & 0 & 0 & 0 \\ 0 & k_{Mg} & 0 & 0 \\ 0 & 0 & k_{Cy} & 0 \\ 0 & 0 & 0 & k_{Ye} \end{pmatrix} \quad (30)$$

[Formula 31]

$$A = \begin{pmatrix} -0.413 & -0.678 & 4.385 \\ -0.040 & -3.590 & 2.085 \\ -0.011 & -2.504 & -1.802 \\ 0.332 & 3.233 & -3.310 \end{pmatrix} \quad (31)$$

-continued

[Formula 32]

$$K = \begin{pmatrix} 1 & 0 & 0 & 0 \\ 0 & 0.814 & 0 & 0 \\ 0 & 0 & 0.730 & 0 \\ 0 & 0 & 0 & 0.598 \end{pmatrix} \quad (32)$$

[Formula 33]

$$A^t = KA = \begin{pmatrix} 1 & 0 & 0 & 0 \\ 0 & 0.814 & 0 & 0 \\ 0 & 0 & 0.730 & 0 \\ 0 & 0 & 0 & 0.598 \end{pmatrix} \begin{pmatrix} -0.413 & -0.678 & 4.385 \\ -0.040 & -3.590 & 2.085 \\ -0.011 & -2.504 & -1.802 \\ 0.332 & 3.233 & -3.310 \end{pmatrix} \quad (33)$$

$$= \begin{pmatrix} -0.413 & -0.678 & 4.385 \\ -0.033 & -2.922 & 1.697 \\ -0.008 & -1.828 & -1.315 \\ 0.109 & 1.933 & -1.979 \end{pmatrix}$$

FIG. 33 shows the spectral sensitivity characteristics in the case of using the complementary color type color filter, and the characteristics of the target bandpass filters and the quasi-bandpass filters found from the above described Formula (27) to Formula (33).

It goes without saying that when the complementary color type filter is used, the S/H circuits shown in FIG. 4 perform sampling for G, Mg, Cy and Ye instead of R, G and B.

When the complementary color type color filter is used, the matrix estimation method shown the Formulae (9) to (18) can be also applied. In this case, when the number of complementary color filters is four, the assumed part in the Formula (14) that the biological spectral reflectance can be approximated by the three basic spectral characteristics is changed to the assumed part that the biological spectral reflectance can be approximated by the four, or four or less basic spectral characteristics. Therefore, in correspondence with this, the dimension for computing the estimation matrix is changed to four from three.

According to the present embodiment, the spectral image in which blood vessel patterns are vividly displayed can be obtained as in the embodiment 1. In the present embodiment, the merit in the case of using the complementary color type color filter can be enjoyed.

According to each of the embodiments described above, the effect of being able to adjust the tissue information at a desired deep portion of a biological tissue based on the spectral image obtained by signal processing to image information in a color tone suitable for observation is obtained.

Each of the embodiments in the present invention is described above, but the present invention may be used by variously combining the above described embodiments, or modifications in the range without departing from the spirit of the present invention are conceivable.

For example, for all the embodiments already described, an operator himself can create new quasi-bandpass filters during clinical examination or at the other timings, and can clinically apply them. Specifically, a design section (not shown) capable of computing and calculating matrix coefficients may be provided at the control unit 42 in FIG. 4, when shown in the embodiment 1.

As a result, by inputting the conditions through a keyboard provided at the endoscope main body shown in FIG. 3, the operator newly designs the quasi-bandpass filters suitable for obtaining the spectral image which the operator wants to know, and by setting the final matrix coefficients (corresponding to each of the elements of the matrix "A'" of the Formula (21) and Formula (33)) obtained by applying the correction coefficients (corresponding to each of the elements of the matrix "K" of the Formula (20) and Formula (32)) to the calculated matrix coefficients (corresponding to each of the elements of the matrix "A" of the Formula (19) and Formula (31)) to the matrix computing section 436 in FIG. 4, the operator can quickly apply the quasi-bandpass filters clinically.

Figure 34:
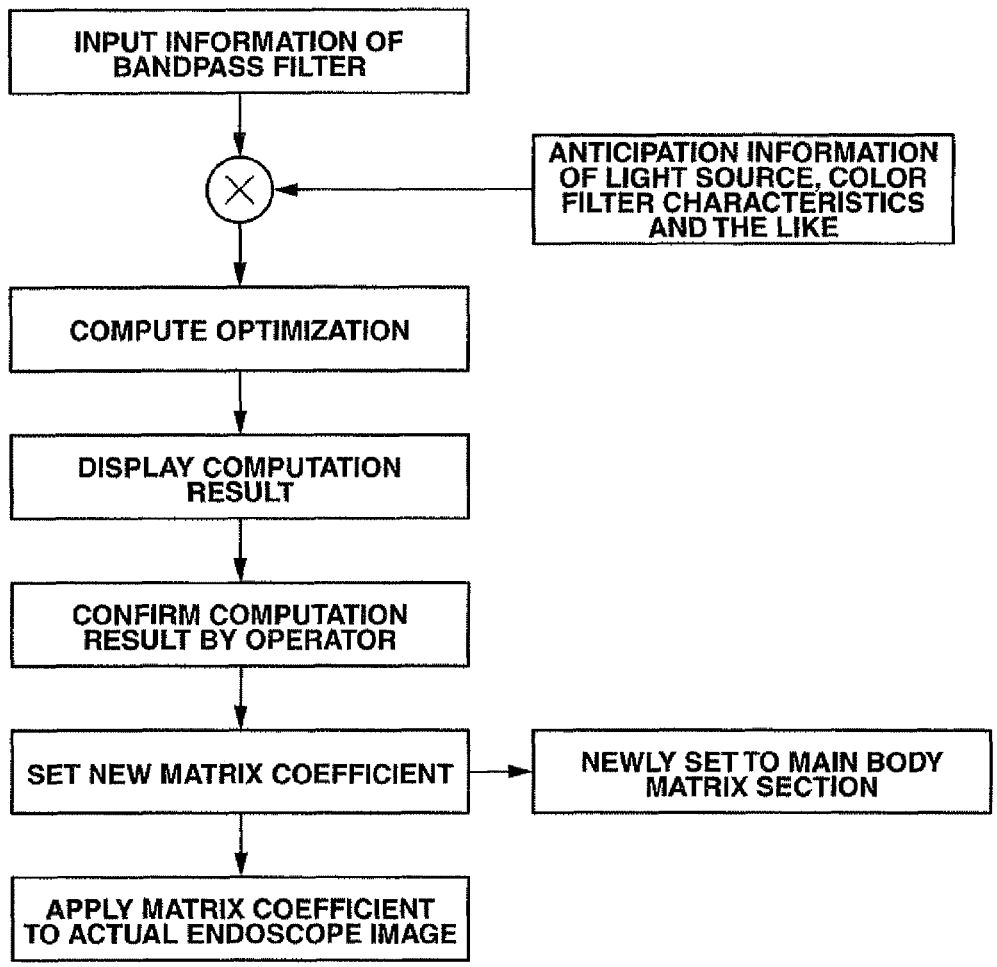
FIG. 34 is a flowchart on an occasion of matrix computation in a modified example according to the present invention.

FIG. 34 shows the flow to the application. The flow will be described in detail. First, the operator inputs the information of the target bandpass filter (for example, wavelength band or the like) through the keyboard or the like. Thereby, with the characteristics or the like of the light source and the color filters already stored in the storage device or the like, the matrix "A'" is calculated, and as shown in FIG. 33, the computation result by the matrix "A'" (quasi-bandpass filters) as well as the characteristics of the target bandpass filters are displayed on the monitor as a spectral diagram.

The operator confirms the computation result, and thereafter, when the operator uses the newly created matrix "A'", the operator performs its setting and creates an actual endoscope image by using the matrix "A'". With this, the newly created matrix "A'" is stored in a predetermined storage device, and can be used again in response to a predetermined operation of the operator.

Thereby, the operator can create new bandpass filters from his own experience or the like without being bound by the existing matrix "A'", and especially in the case of use for research, a high effect is obtained.

Embodiment 7

FIGS. 38 to 41 relate to a biological observation apparatus of an embodiment 7 of the present invention. Since the embodiment 7 is substantially the same as the embodiment 1, only the point differing from the embodiment 1 will be described, and explanation of the same components will be omitted by assigning them with the same reference numerals and characters.

Figure 38:
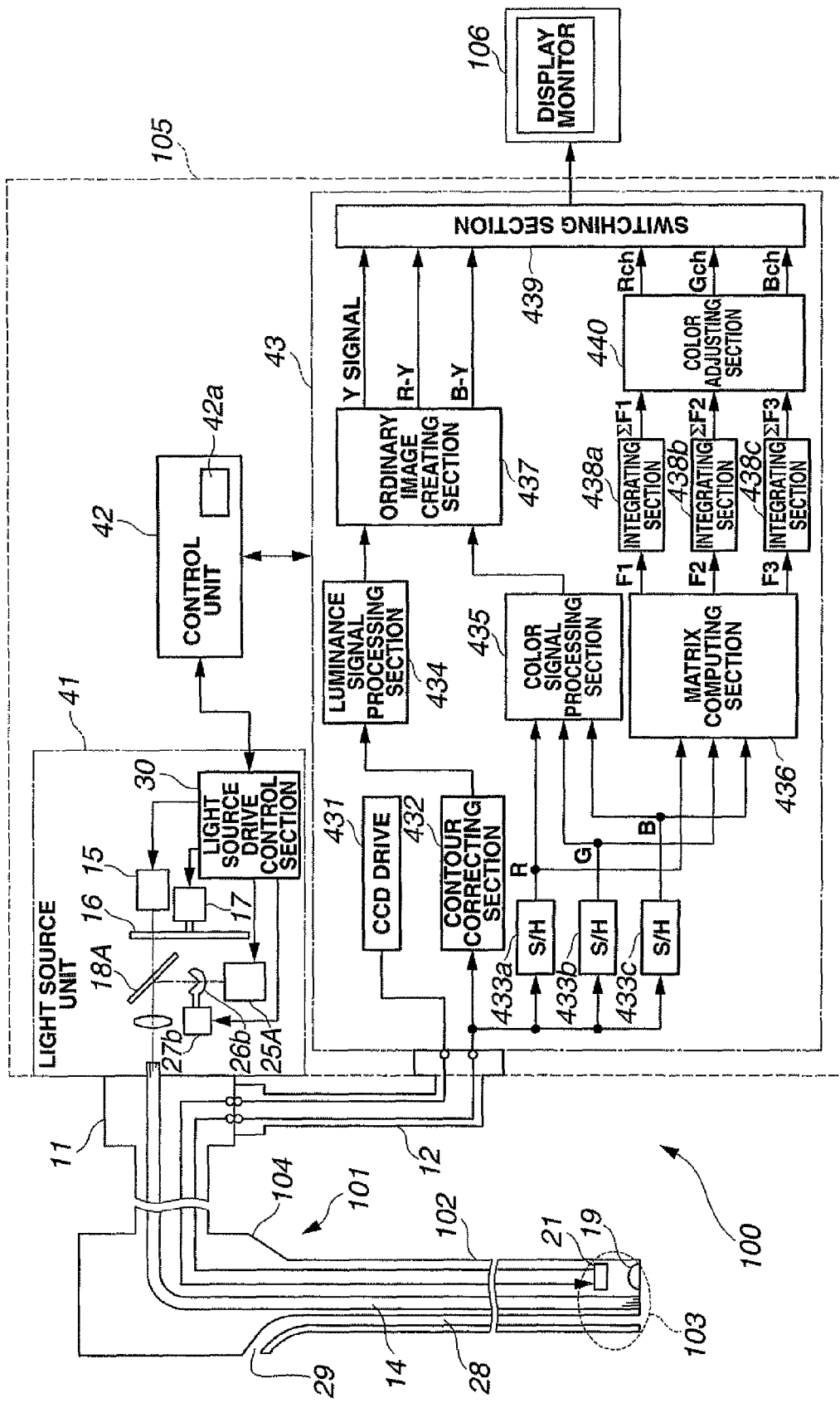
FIG. 38 is a block diagram showing a configuration of an electronic endoscope apparatus according to an embodiment 7 of the present embodiment.
Figure 39:
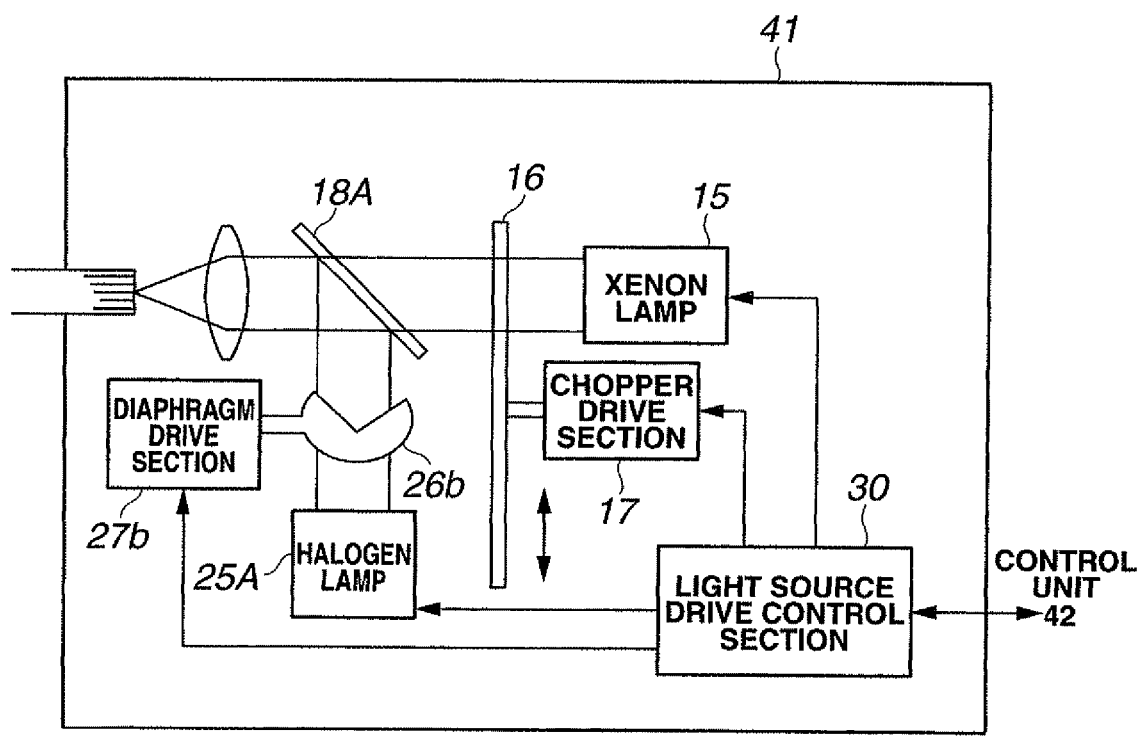
FIG. 39 is a block diagram showing a configuration of a light source unit of FIG. 38.
Figure 40:
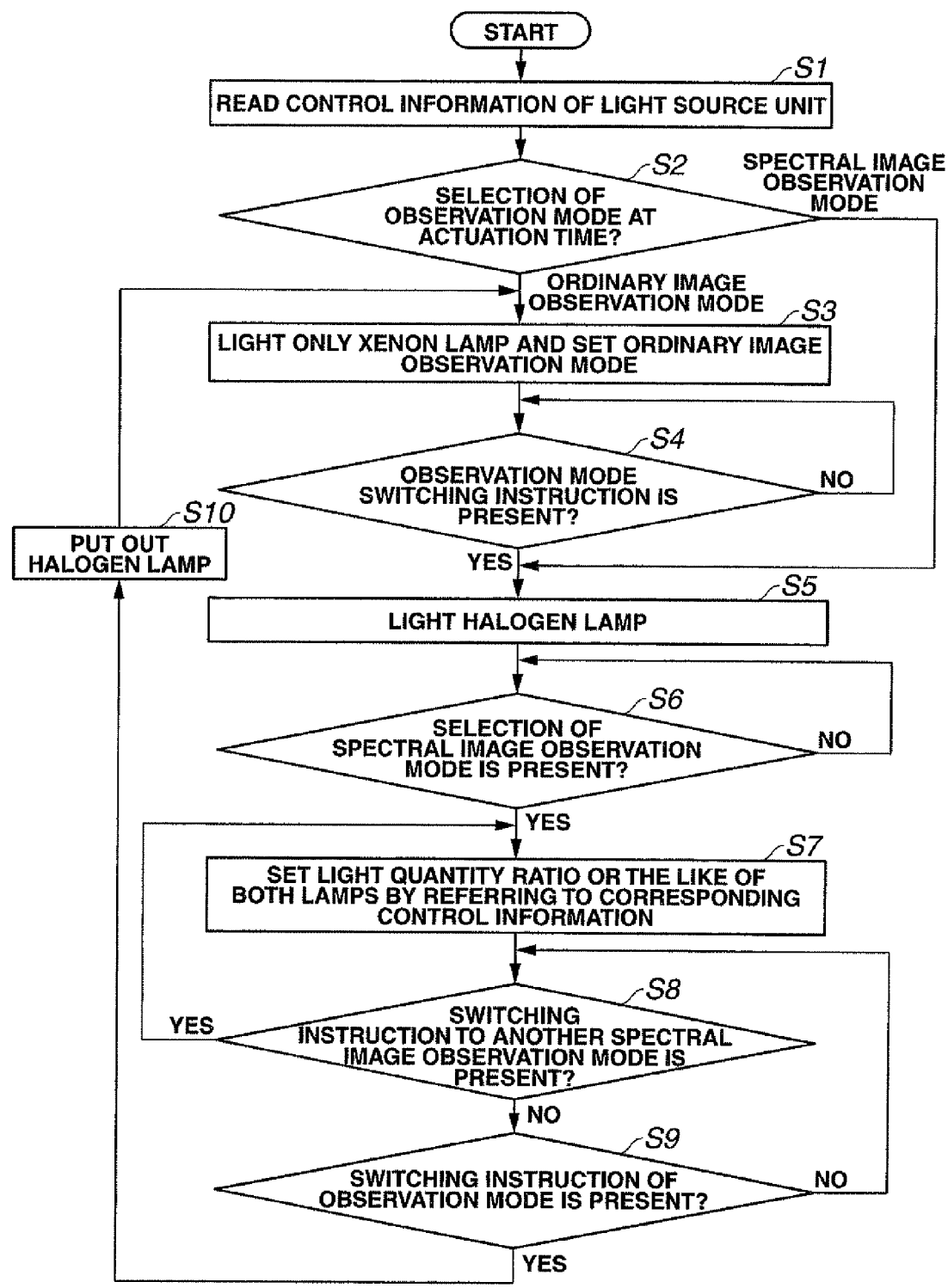
FIG. 40 is a flowchart showing an operation of the embodiment 7.
Figure 41:
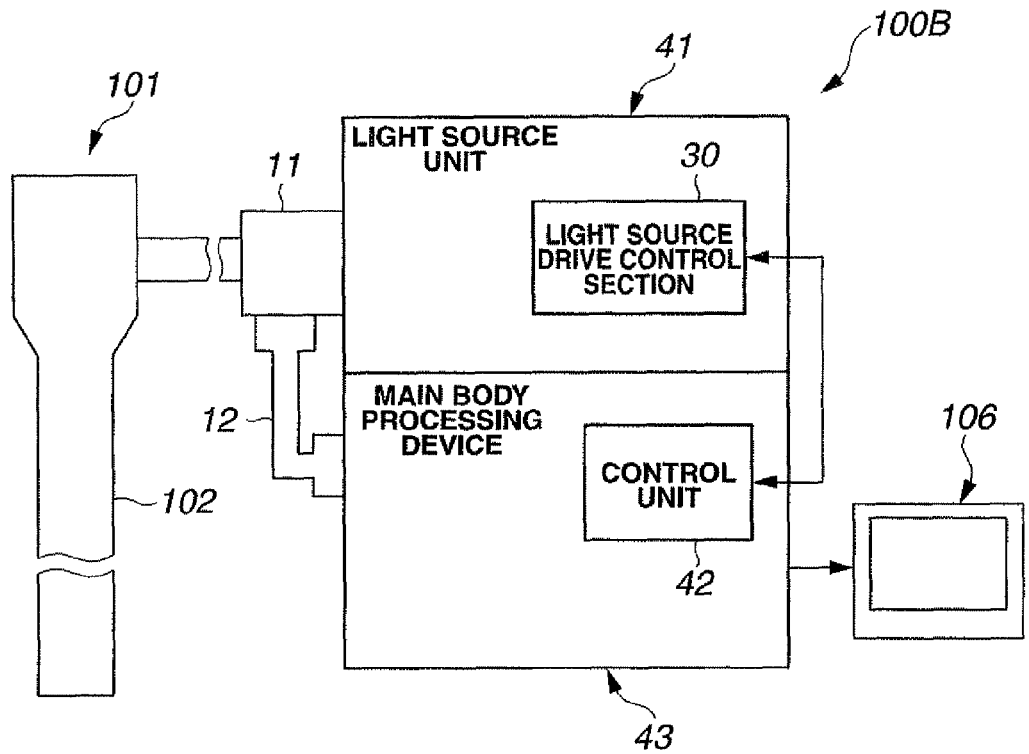
FIG. 41 is a block diagram of a configuration of an electronic endoscope apparatus of a modified example of the embodiment 7.

FIG. 38 is a block diagram showing a configuration of an electronic endoscope apparatus of the present embodiment. FIG. 39 is a block diagram showing a configuration of a light source unit of FIG. 38. FIG. 40 is a flowchart showing an operation of the embodiment including the creating function of the spectral image of FIG. 24 and the like. FIG. 41 is a block diagram of an electronic endoscope of a modified example.

As shown in FIG. 3, the electronic endoscope apparatus 100 has the electronic endoscope (abbreviated as the scope) 101 including the illumination unit and the image pickup unit, the endoscope main body 105 to which the endoscope 101 is connected, and which controls the illumination unit and the image pickup unit, and the display monitor 106 which displays and outputs a biological signal outputted from the endoscope apparatus main body 105.

As shown in FIGS. 38 and 39, the light source unit 41 is connected to the control unit 42 and the endoscope 101, and performs irradiation of white light (including the case of incomplete white light) with a predetermined light quantity based on the signal from the control unit 42.

The light source unit 41 has, for example, the xenon lamp 15 as the first light source, the chopper 16 for adjusting the light quantity, and the chopper drive section 17 for driving the chopper 16. The light from the xenon lamp 15 passes through the chopper 16, transmitting through a half mirror 18A disposed on its optical path, and thereafter, is gathered by a condenser lens to be incident on the incidence end of the light guide 14 of the endoscope 101.

In the present embodiment, the light source unit 41 is provided with, for example, a halogen lamp 25A as a second light source differing in spectral characteristic from the above described first light source, a diaphragm 26b which adjusts a light quantity of the halogen lamp 25A, and a diaphragm drive section 27b which drives the diaphragm 26b.

The illumination light of the halogen lamp 25A transmits through the diaphragm 26b. Thereafter, part of the illumination light is reflected by the half mirror 18A, and gathered by the condenser lens to be incident on the incidence end of the light guide 14 of the endoscope 101.

A light source drive control section 30 is provided in the light source unit 41, and the light source drive control section 30 performs lighting and extinguishing of both the lamps 15 and 25A and control operations of the chopper drive section 17 and the diaphragm drive section 27b.

The light source drive control section 30 is also connected to the control unit 42 so as to be able to control the illumination light supplied to the light guide 14 of the endoscope 101 by the light source unit 41 in accordance with the observation mode via the control unit 42. The spectral distribution of the xenon lamp 15 is shown in the drawing with the case of a mercury lamp which is adopted in an embodiment 8 which will be described later. The halogen lamp 25A has spectral distribution in a wide band at a color temperature lower than the xenon lamp 15.

In the present embodiment, for example, in the ordinary image observation mode, illumination is performed by lighting only, for example, the xenon lamp 15 side, and in the spectral image observation mode, illumination is performed by lighting both the lamps 15 and 25A.

A more desirable spectral image signal is obtained as will be described later. As the chopper 16 which is disposed before the xenon lamp 15 and performs light quantity adjustment, the one disclosed in, for example, Japanese Patent Laid-Open No. 2003-93336 can be adopted, and since the detailed configuration is described in Japanese Patent Laid-Open No. 2003-93336, and therefore, its explanation will be omitted.

The chopper drive section 17 is configured to be movable in a direction orthogonal to the optical path of the light from the xenon lamp 15 as shown by the arrows in FIG. 39. When the distance from the optical path becomes large due to its movement, the notch portion where the luminous flux can pass becomes long. Therefore, irradiation time becomes long, and the illumination light quantity can be made large.

Since a spectral image which is newly created is likely to be insufficient as S/N, and when any signal required for creation is saturated, correct computation is not performed as described above, the illumination light quantity needs to be controlled. The light quantity adjustment is carried out by the chopper 16 and the chopper drive section 17 with only one lamp as in Japanese Patent Laid-Open No. 2003-93336.

On the other hand, in the present embodiment, the two light sources differing in the spectral characteristic are included, and therefore, especially when the spectral image observation mode is set, a spectral image signal is created and the spectral image is displayed on the display monitor 106, it is made possible to create a more suitable spectral image by using the two light sources.

In this case, information of the ratio of the illumination light quantities which is supplied to the light guide 14 from both the lamps 15 and 25A and the maximum light quantity when illumination is performed in the spectral image observation mode is stored in a nonvolatile memory 42a such as an EEPROM provided in the control unit 42, for example. When the spectral image observation mode is set, the control unit 42 refers to the information and controls the illumination light which is supplied to the light guide 14 from the light source unit 41 via the light source drive control section 30.

A color filter 22a which optically performs color separation is provided on the image pickup surface of the CCD 21, and arrangement of the color filter 22a is as shown in FIG. 6 as described above. The spectral sensitivity characteristics of R, G and B filters which configure the color filter 22a are shown by the solid lines in FIG. 7.

Explaining the operation of the light source unit 41 when observing an ordinary image first, the light source drive control section 30 operates only the xenon lamp 15 side of the light source unit 41 based on the control signal from the control unit 42. In this case, the chopper drive section 17 is set at a predetermined position to rotate the chopper 16. The luminous flux from the xenon lamp 15 passes through the notch portion of the chopper 16, and is gathered on the incidence end of the light guide 14 which is an optical fiber bundle provided in the connector 11 at the connecting portion of the scope 101 and the light source unit 41 by the condenser lens. The ordinary image is observed by the same observation operation of the ordinary image in the above described embodiment 1.

Next, when observing a spectral image, the operator performs instruction for observing a spectral image from the ordinary image by operating the keyboard provided at the endoscope apparatus main body 105, a scope switch not shown provided at the operation portion 104 of the endoscope 101, the front panel of the main body processing device 43, or the like. At this time, the control unit 42 changes the control states of the light source unit 41 and the main body processing device 43.

More specifically, the control unit 42 refers to the control information of the memory 42a, sends the control signal to the light source drive control section 30 of the light source unit 41, and also lights the halogen lamp 25A. The control unit 42 controls the drive of the chopper 16 and the diaphragm 26b so that the illumination light quantity by both the lamps 15 and 25A becomes a proper light quantity.

As described above, it is undesirable that the output from the CCD 21 is saturated, and therefore, at the time of observing a spectral image, the maximum value of the illumination light quantity is made small as compared with the time of observing an ordinary image. The control unit 42 controls the light quantity so that the output signal from the CCD 21 is not saturated, and sets the illumination light quantity in the range in which the output signal is not saturated.

As the control change for the main body processing device 43 by the control unit 42, the signal outputted from the switching section 439 is switched to the output of the color adjusting section 440 from the output of the ordinary image creating section 437. Further, the outputs of the S/H circuits 433a to 433c are subjected to amplification and addition processing in the matrix computing section 436, then, are outputted to the integrating sections 438a to 438c in accordance with the respective bands, and after being subjected to the integration processing, outputted to the color adjusting section 440. When the illumination light quantity is made small with the chopper 16 and the diaphragm 26b, the signal intensities can be increased by storing and integrating the signals in the integrating sections 438a to 438c as shown in FIG. 2, and the spectral image with the S/N enhanced can be obtained.

Concrete matrix processing of the matrix computing section 436 in the present embodiment will be described hereinafter. In order to describe superiority of the case of using the two lamps 15 and 25B having different spectral characteristics according to the present embodiment, the case corresponding to the case of Japanese Patent Laid-Open No. 2003-93336 of the case of using only one lamp 15 will be described first.

In the case of only the lamp 15, when the bandpass filters (hereinafter, called the quasi-bandpass filters) close to the ideal narrow band bandpass filters F1 to F3 shown in FIG. 7 (in this case, the respective transmission wavelength regions are set at F1: 590 nm to 620 nm, F2: 520 nm to 560 nm, F3: 400 nm to 440 nm) are to be created from the spectral sensitivity characteristics of the ROB color filters shown by the solid lines in FIG. 7, the matrix of the above described Formula (19) is the optimal from the contents shown in the above described Formula (1) to Formula (5).

Further, when correction is performed from the contents shown in the Formula (6) and Formula (7), the correction coefficients of the above described Formula (20) are obtained.

The anticipation information that the spectrum $S(\lambda)$ of the light source shown in the Formula (6) is the one shown in FIG. 9 in the case of only the xenon lamp 15, for example, and that the reflection spectrum $H(\lambda)$ of the living body shown in the Formula (7), to which attention is paid is the one shown in FIG. 10 is used.

Accordingly, the processing which s performed in the matrix computing section 436 mathematically has the same value as the matrix computation of the above described Formula (21).

By performing the matrix computation, the quasi-filter characteristics (shown in FIG. 7 as the characteristics of the filters quasi—F1 to F3) are obtained. Specifically, the above described matrix processing creates spectral image signals by using the quasi-bandpass filters (matrix) which are created in advance as described above for the color image signals.

In this case, as shown by the thick broken lines of FIG. 7, in the created quasi-bandpass filters (matrix), alienation of the one at the long wavelength side (F1) from the ideal bandpass filter is especially large.

Therefore, in the present embodiment, at the time of the spectral image observation mode, the halogen lamp 25A which is lower in color temperature than the xenon lamp 15, specifically, has the light emission characteristic shifted to the long wavelength side is also lit, and the processing of creating the quasi-bandpass filters (matrix) is performed by using the illumination light by both the lamps 15 and 25A.

Specifically, by raising the luminance level at the long wavelength side in the illumination light, the value of the R signal at the long wavelength side is relatively made large, so that alienation of the quasi-bandpass filter (matrix) at the long wavelength side can be more improved than the case of using only one xenon lamp 15.

The endoscope image created by using the quasi-filter characteristics in this manner and the structure of the biological tissue to be observed are as described above by using FIGS. 11 to 26.

In order to be able to cope with any spectral image observation mode of the above described embodiments, first modified example, second modified example and third modified example, the information suitable for the respective spectral image observation modes may be stored in, for example, the memory 42a of the control unit 42.

When the mode is switched to the spectral image observation mode, the last spectral image observation mode that was used before, for example, is set, and the other spectral image observation modes may be selected and used (switch use) by selection of the user.

FIG. 40 shows an operation of observing a living body in the spectral image observation mode corresponding to such a case. In the following description, the spectral image observation mode in the above described embodiments, and the spectral image observation modes of the first to the third modified examples will be described as the first to the fourth spectral image observation modes.

When the power supply is turned on and the electronic endoscope apparatus 100 is in the operating state, the control unit 42 reads the program information of the memory 42a and starts the control operation of the electronic endoscope apparatus 100 as shown in step S1. The control unit 42 also reads the control information for the light source unit 41 at the time of each of the observation modes of the memory 42a.

Subsequently, as shown in step S2, the control unit 42 finds selection of the observation mode at the time of actuation. For example, the control unit 42 displays a menu screen and performs display for finding the selection of the observation mode at the time of actuation on the menu screen. Subsequently, the user performs selection of the observation mode at the time of actuation.

When the ordinary image observation mode is selected, the control unit 42 sends a control signal to the light source control section 30 based on the information read from the memory 42a, lights only the xenon lamp 15 and sets the ordinary image observation mode, as shown in step S3. Subsequently, the user observes a biological tissue as a test subject in the ordinary image observation mode.

When the ordinary image observation mode starts, the control unit 42 is in the state of waiting for a switching instruction of the observation mode as shown in step S4. When the switching instruction of the observation mode is made by operating the change-over switch or the like of the observation mode provided at the endoscope 101 or the like, the control unit 42 sends a control signal to the light source drive control section 30 based on the information read from the memory 42a and lights the halogen lamp 25A, as shown in step S5.

As shown in step S6, the control unit 42 finds the selection of in which spectral image observation mode observation is to be performed. The user desires to perform observation and selects the spectral image observation mode. Then, it is assumed that the user selects the $k^{th}$ (k=1 to 4) spectral image observation mode. Then, as shown in step S7, the control unit 42 refers to the control information corresponding to the $k^{th}$ spectral image observation mode, sets the light quantity ratio of the xenon lamp 15 and the halogen lamp 25A, and sets the maximum light quantity.

Linked to this, the control unit 42 selects and sets the coefficients of the matrix computing section 436 to be linked to the selection of the $k^{th}$ spectral image observation mode, so that the spectral image signals in the case of the $k^{th}$ spectral image observation mode can be created with high precision by the selection and setting of the linked coefficients.

Subsequently, the user can perform observation in the $k^{th}$ spectral image observation mode. When the control unit 42 sets the $k^{th}$ spectral image observation mode, the control unit 42 is in the state of monitoring switching to the other spectral image observation modes as shown in step S8. When the operation of switching to the $m^{th}$ (m≠k) spectral image observation mode is performed, the control unit 42 refers to the information corresponding to the selected $m^{th}$ spectral image observation mode as shown in step S7, sets the light quantity ratio of the xenon lamp 15 and the halogen lamp 25A and sets the maximum light quantity.

When a switching operation to the other spectral image observation modes is not performed in step S8, the control unit 42 determines whether the switching instruction of the observation mode is performed or not as shown in step S9.

When the switching instruction of the observation mode is not performed, the flow returns to step S8. When the switching instruction of the observation mode is performed, the control unit 42 performs extinguishing control of the halogen lamp 25A as shown in step S10, and the flow returns to step S3.

In the above described control processing, control of closing the diaphragm 26b may be performed instead of extinguishing the halogen lamp 25A to enhance responsiveness at the switching time of the observation mode.

According to the present embodiment, the effect of the embodiment 1 can be made to occur, and a plurality of light sources having different emission characteristics are used for obtaining a spectral image. Therefore, a spectral image with higher precision than in the case of using only one light source can be obtained.

The matrix computing section 436 in the present embodiment may have the configuration as shown in FIG. 28 as a modified example.

The electronic endoscope apparatus 100 of the embodiment 1 shows the configuration in which the light source unit 41 generating illumination light and the main body processing device 43 performing signal processing are integrated, but as in an electronic endoscope apparatus 100B shown in FIG. 41, the light source unit 41 and the main body processing device 43 may be configured to be separate. In the configuration example of FIG. 41, the control unit 42 is provided in the main body processing device 43 so as to be able to send and receive a control signal by the light source drive control section 30 in the light source unit 41 through a communication cable.

The present modified example has the substantially same operational effect as in the case of the embodiment 1 shown in FIG. 4.

Embodiment 8

Next, an embodiment 8 of the present invention will be described with reference to FIGS. 42 to 45. An electronic endoscope apparatus according to the present embodiment has a configuration in which the light source unit 41 of FIG. 38 is changed to a light source unit 41B shown in FIG. 42.

The light source unit 41B adopts an ultra high pressure mercury lamp (hereinafter, simply abbreviated as a mercury lamp) 35 having a bright line spectrum instead of the halogen lamp 25 used as the second light source in the light source unit 41 shown in FIG. 39.

In this embodiment, a diaphragm 26a is disposed between the xenon lamp 15 and the half mirror 18A, and an opening amount of the diaphragm 26a is variably driven by a diaphragm drive section 27a.

After the light quantity of the light of the xenon lamp 15 is adjusted by the diaphragm 26a, the light is incident on the half mirror 18A, and the light quantity of the light of the mercury lamp 35 is adjusted by the diaphragm 26b and is incident on the half mirror 18A. Thus, a light mixing section 36 which mixes light with the light from the xenon lamp 15 is formed by the half mirror 18A.

The xenon lamp 15 and the mercury lamp 35 are controlled to be lit and extinguished by the light source drive control section 30 via an internal lighting drive circuit, and the drive operations of the diaphragm drive sections 27a and 27b are also controlled by the light source drive control section 30.

Figure 43:
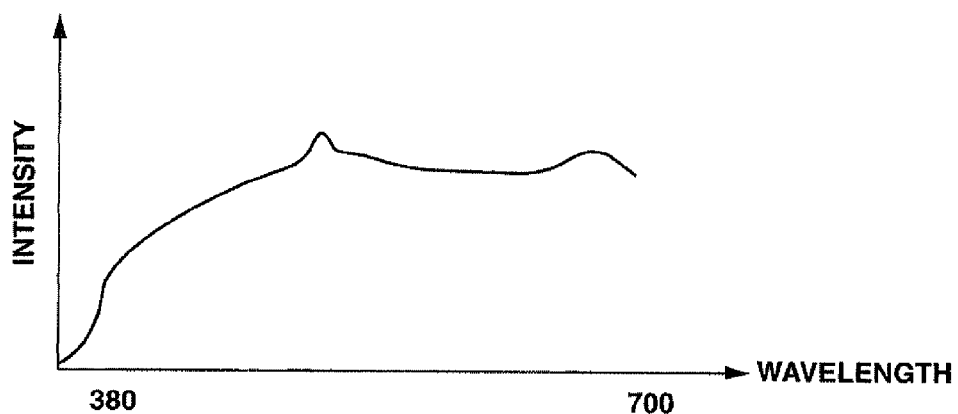
FIG. 43 is a characteristic chart showing a spectral characteristic of light emission of a xenon lamp.
Figure 44:
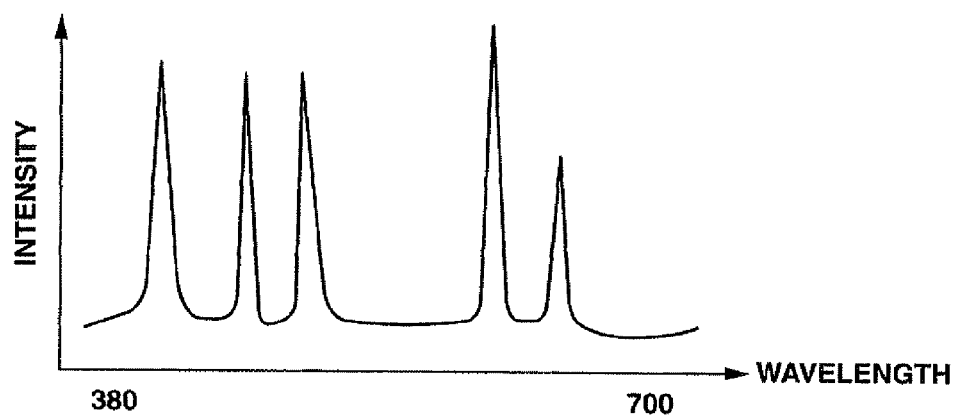
FIG. 44 is a characteristic chart showing a spectral characteristic of light emission of a mercury lamp.

FIG. 43 shows the spectral characteristic of emission of the xenon lamp 15, which has broad intensity distribution over the visible region. FIG. 44 shows the emission characteristic of the mercury lamp 35, which has broad intensity distribution over a visible region and has a plurality of bright line spectrums.

In the present embodiment, in the normal image observation mode, only the xenon lamp 15 is lit, and an ordinary image is displayed on the display monitor 106.

Figure 45:
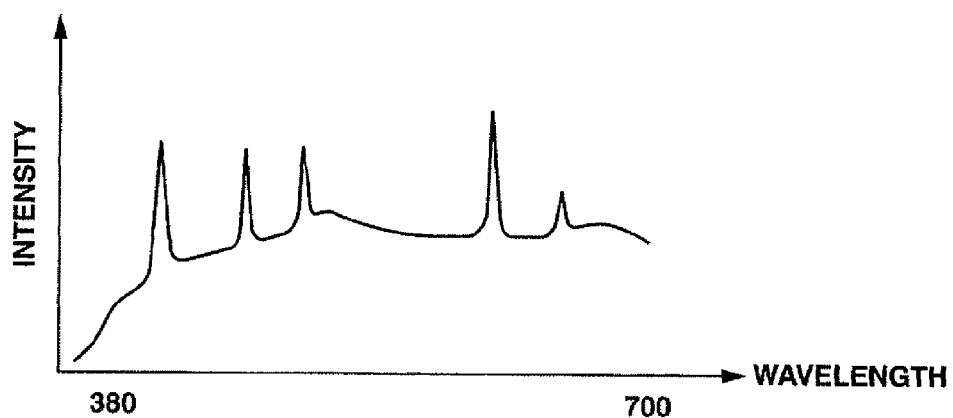
FIG. 45 is a diagram showing an intensity distribution characteristic example of illumination light outputted by a light mixing section with respect to a wavelength at a time of a spectral image observation mode.

On the other hand, in the spectral image observation mode, the xenon lamp 15 and the mercury lamp 35 are lit, the light quantity ratio by both the lamps 15 and 35 are set on this occasion, illumination light with the total light quantity limited, for example, the illumination light in which each light is mixed by the light mixing section 36 as shown in FIG. 45 is supplied to the light guide 14, and a spectral image is displayed on the display monitor 106.

According to the present embodiment, at the time of the spectral image observation mode, by adopting the illumination light having a plurality of bright line spectrums, the signal intensity in each of the bright line spectrum portions can be made large, and the spectral image signal can be calculated with higher precision than in the case of having no bright line spectrum. Thus, a spectral image with high reliability can be obtained.

Embodiment 9

Figure 46:
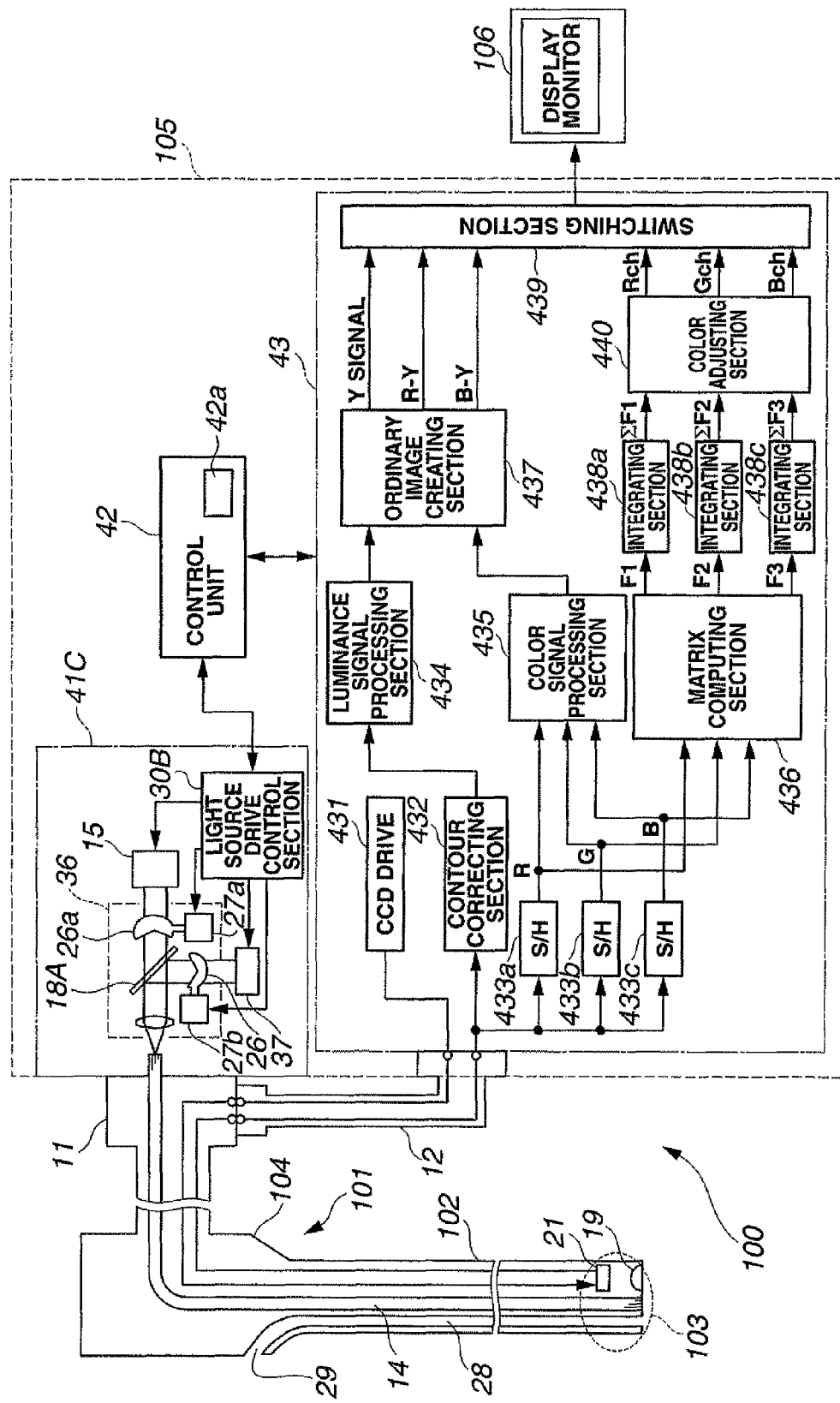
FIG. 46 is a block diagram showing a configuration of an electronic endoscope apparatus according to an embodiment 9.

Next, an embodiment 9 of the present invention will be described with reference to FIGS. 46 to 51. The electronic endoscope apparatus 100 according to the present embodiment shown in FIG. 46 has a configuration in which the light source unit 41 of FIG. 46 is changed to a light source unit 41C shown in FIG. 47.

Figure 42:
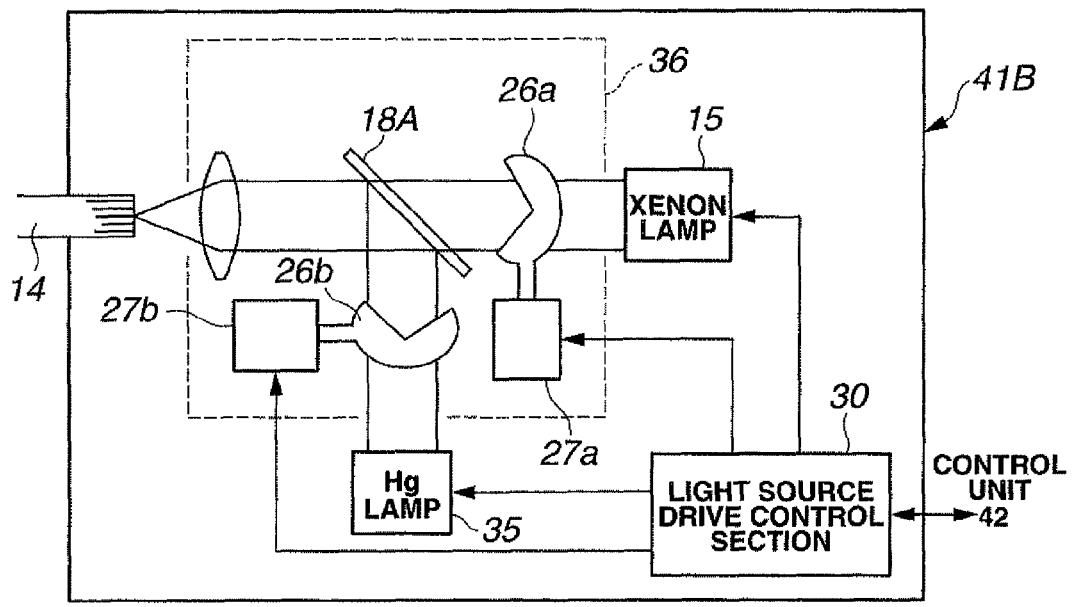
FIG. 42 is a block diagram showing a configuration of a light source unit in an embodiment 8.
Figure 47:
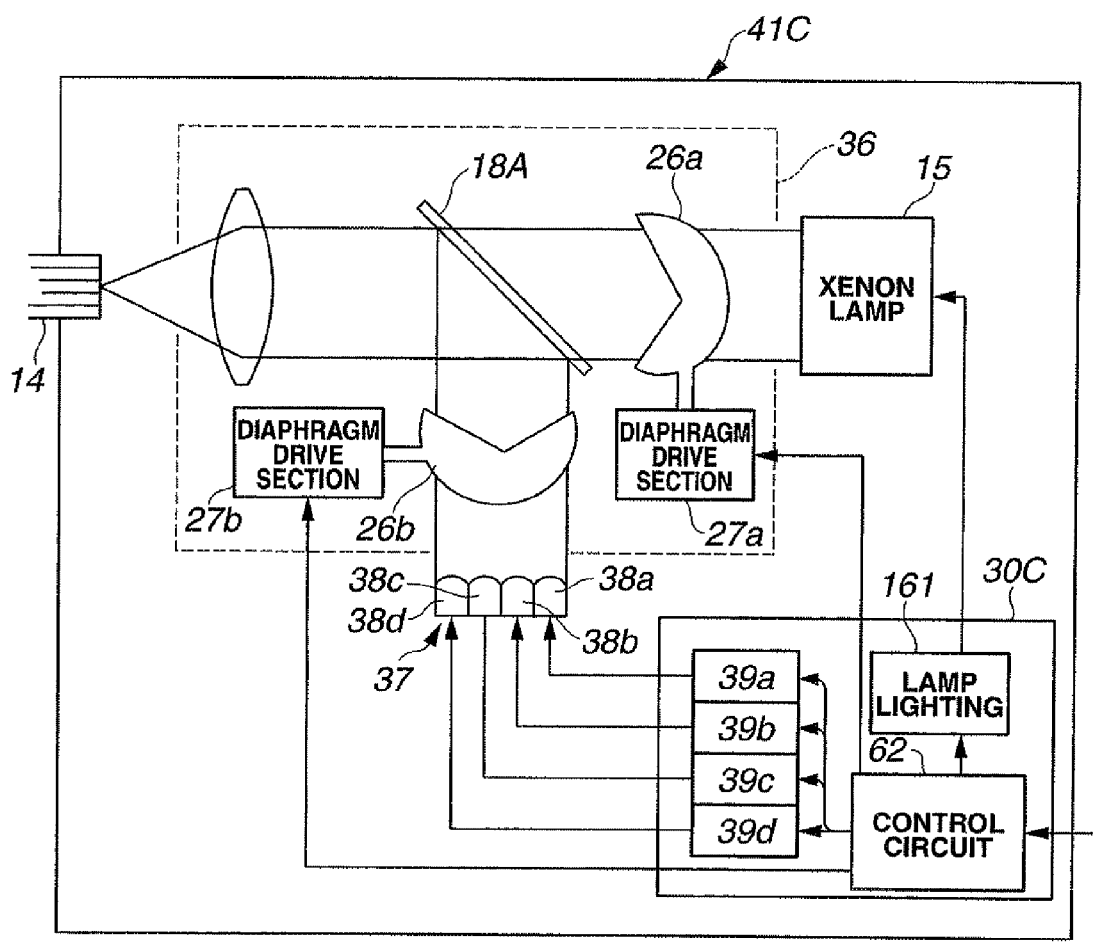
FIG. 47 is a block diagram showing a configuration of a light source unit in FIG. 46.

As shown in FIG. 47, the light source unit 41C adopts a light emitting diode section (LED section) 37 as a semiconductor light source instead of the mercury lamp 35 in the light source unit 41B shown in FIG. 42. The LED section 37 is configured by a plurality of, more specifically, four LEDs 38a to 39d having a plurality of emission spectrums.

Figure 48:
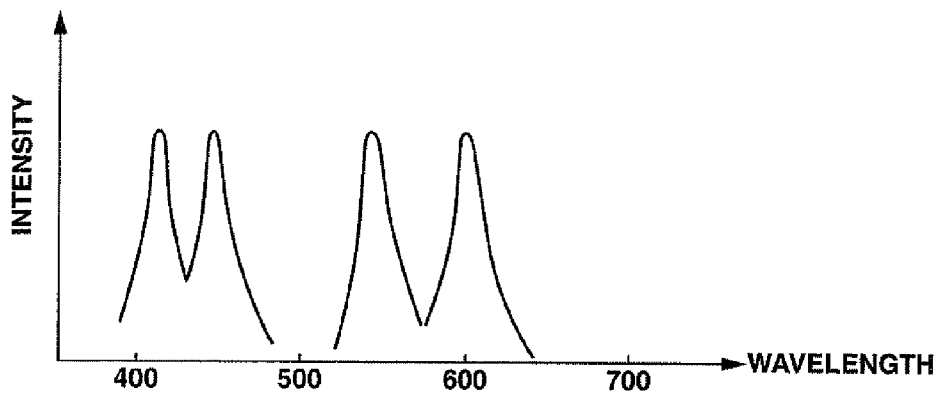
FIG. 48 is a diagram showing a spectral characteristic example of light emission by a plurality of LEDs of an LED section of FIG. 47.

FIG. 48 shows the emission spectrums (spectral characteristics) of the LED 38a to 39d. The emission spectrums in this case have bright line spectrums or spectrums which are slightly broader than the bright line spectrums in the vicinity of the wavelength of the spectrum image signal to be created. The case of four is shown, but the number of emission spectrums is not limited to four.

In the present embodiment, a light source drive control section 30C is configured by LED drivers 39a to 39d which drive a plurality of LEDs 38a to 38d configuring the LED section 37 to emit light, a lamp lighting circuit 161 which lights the xenon lamp 15, and a control circuit 62 which controls the LED drivers 39a to 39d, the lamp lighting circuit 161 and the diaphragm drive sections 27a and 27b.

The control circuit 62 controls the illumination light which is supplied to the light guide 14 from the light mixing section 36 of the light source unit 41C in correspondence with the control signal from the control unit 42.

In the present embodiment, in the ordinary image observation mode, only the xenon lamp 15 is lit, and an ordinary image is displayed on the display monitor 106.

Figure 49:
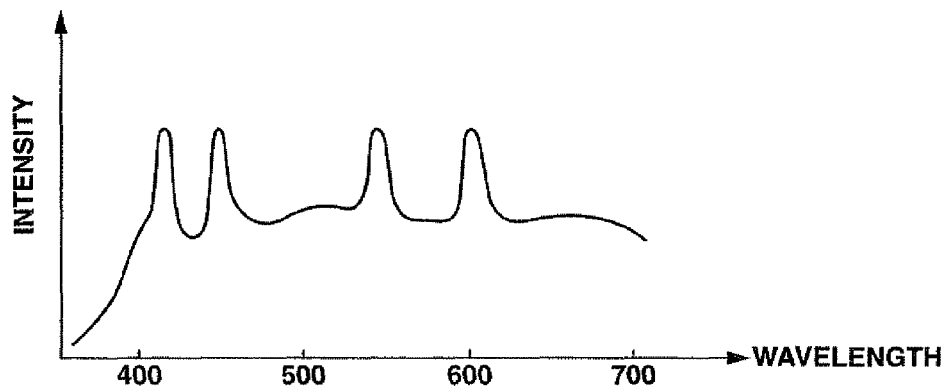
FIG. 49 is a diagram showing an emission characteristic example of illumination light at the time of the spectral image observation mode in the embodiment 9.

On the other hand, in the spectral image observation mode, the xenon lamp 15 and the LEDs 38a to 38d are lit, and the light quantity ratio by the xenon lamp 15 and the LEDs 38a to 39d is set on this occasion, the illumination light with the total light quantity limited, for example, the illumination light in which each light is mixed by the light mixing section 36 as shown in FIG. 49 is supplied to the light guide 14, and a spectral image is displayed on the display monitor 106.

According to the present embodiment, the effect similar to the embodiment 8 is provided. Specifically, at the time of the spectral image observation mode, by adopting the illumination light having the intensity distribution near a plurality of bright line spectrums, signal intensity at the wavelength portion in the case of creating a spectral image signal can be made large, and the spectral image signal can be calculated with higher precision than in the case of the illumination light which does not have such a characteristic.

By selectively using the LEDs in accordance with the wavelength of the spectral image signal to be calculated, light can be emitted in a bright line spectrum state with that wavelength, and the spectral image signal with high precision can be obtained.

Figure 50:
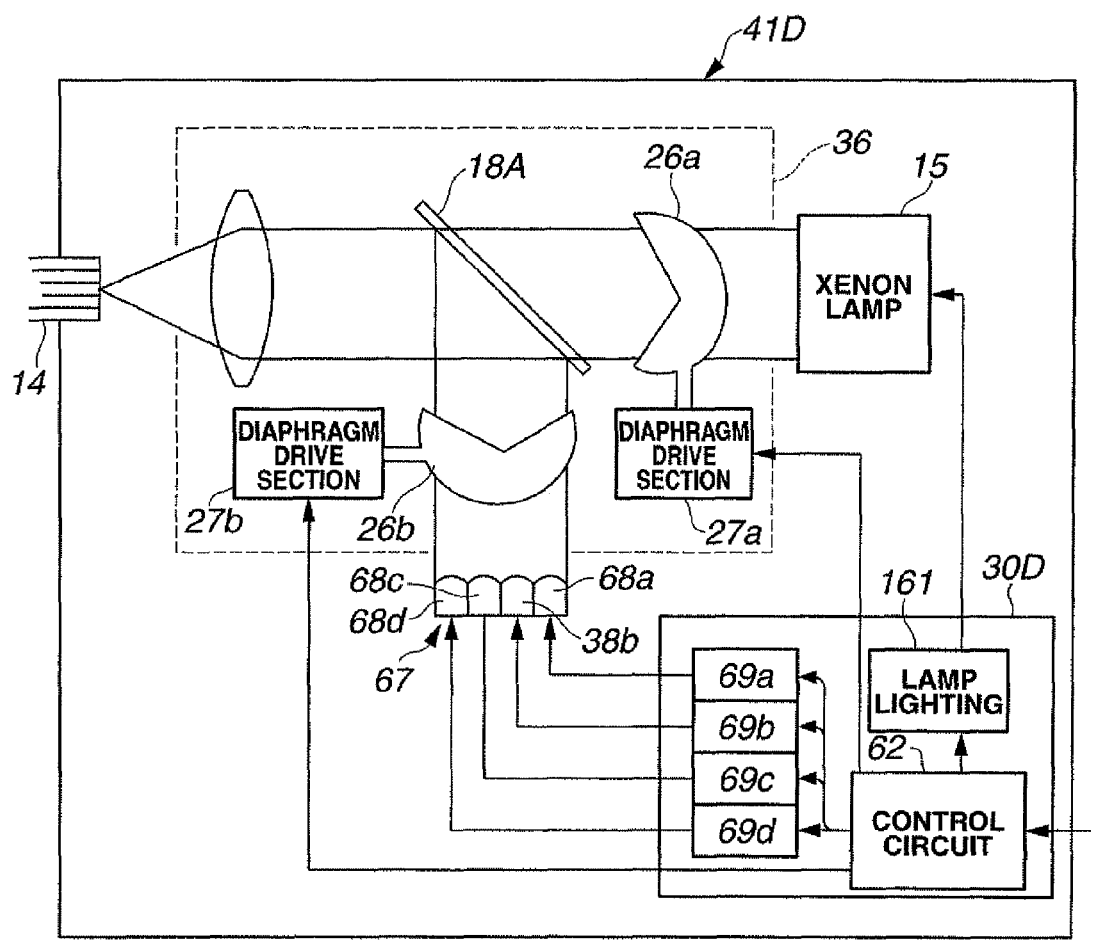
FIG. 50 is a block diagram showing a configuration of a light source unit in a modified example of the embodiment 9.

FIG. 50 shows a light source unit 41D in a modified example. The present modified example adopts a laser diode (hereinafter, abbreviated as an LD) section 67 instead of the LED section 37 in the light source unit 41C of FIG. 47.

Specifically, LDs 68a to 68d are adopted instead of the LEDs 38a to 38d in FIG. 47. Further, in the control circuit 30C in FIG. 47, LD drivers 69a to 69d are adopted instead of the LED drivers 39a to 39d.

The LD 68a to 68d emit light each having width of an emission spectrum narrower than the width of the emission spectrum of each of the LEDs 38a to 38d. As in the embodiment 7, at the time of the ordinary image observation mode, only the xenon lamp 15 is used as the illumination light, and at the time of the spectral image observation mode, the LDs 68a to 68d are lit with the xenon lamp 15.

FIG. 51A shows the spectral characteristic example of the illumination light which is supplied to the light guide 14 from the light mixing section 36, which is the characteristic having a bright line spectrum having width of an emission spectrum narrower than the width of the emission spectrum by each of the LEDs 38a to 38d in the illumination light in FIG. 49.

According to the present modified example, the effect similar to that of the embodiment 7 is provided. Specifically, when a spectral image signal with a desired wavelength is to be obtained, by using the illumination light in which the luminance level is in a bright line shape and becomes large in that wavelength portion, the signal level with the wavelength can be made large, and the desired spectral image signal can be calculated with higher precision.

As shown in FIGS. 51B and 51C, it may be made possible for a user to change (select) the spectral characteristic of the illumination light which is supplied to the light guide 14 from the light mixing section 36 with a scope switch not shown or the like.

In FIGS. 51B and 51C, the number of LDs to be lit is changed (selected). FIG. 51B shows an example of simply changing the number of LDs to be lit in FIG. 51A, but FIG. 51C corresponds to the case where only the LDs are practically lit and the xenon lamp 15 is extinguished.

The case of FIG. 51B is effective in the case of creating spectral image signals in the two bright line spectrum portions. According to FIG. 51C, only light in the two bright line spectrum portions exist, and therefore, spectral image signals with higher precision can be created. FIG. 51C is effective when the spectral image signals at two wavelengths are obtained, and when the spectral image signal at other wavelengths is to be obtained, an LD having a base line spectrum at the wavelength corresponding to the spectral image signal is caused to emit light. The explanation is made with the case of the LDs, but this may be also applied to the case of LEDs.

Specifically, when a plurality of LEDs 38a to 38d, LDs 68a to 68d and the like (the number of them may be made larger) are lit and used in the spectral image observation mode, the LEDs 38a to 38d, the LDs 68a to 68d and the like to be lit may be selected in accordance with the spectral image signal to be calculated. Thus, a desired spectral image can be obtained with high precision with respect to the wavelengths in a wider range.

In the above described embodiments, as the color filter 22a of the CCD 21, the one shown in FIG. 6 is adopted, but as a modified example, the color filter shown in FIG. 32 may be adopted. Since the configuration of the electronic endoscope apparatus in this case is substantially the same as in the embodiment 7, only the different point will be described, and the explanation of the same components will be omitted by assigning them with the same reference numerals and characters as in the embodiment 7.

Whereas in the embodiment 7, the RGB primary color type color filter is used as shown in FIG. 6, a complementary color type color filter is used in the present embodiment.

In this case, all the pixels of the CCD 21 are read, and the image from each color filter is subjected to signal processing or image processing. When the Formula (1) to Formula (8) and the Formula (19) to Formula (21) about the primary color type color filter are modified for the case of the complementary color type color filter, the above described Formula (27) to Formula (33) are obtained. The Formula (27) to Formula (33) are as described above, and the explanation of them will be omitted. The spectral sensitivity characteristics in the case of using the complementary type color filter and the characteristics of the target bandpass filters and the quasi-bandpass filters found by the above described Formula (27) to Formula (33) are as shown in the above described FIG. 33.

It goes without saying that in the present embodiment, in the case of using the complementary color type filter, the S/H circuits shown in FIG. 4 perform sampling for G, Mg, Cy and Ye instead of R, G and B.

When the complementary color type color filter is used, the matrix estimation method shown in the above described Formulae (9) to (18) can be also applied. In this case, when the number of complementary color filters is four, the assumed part in the Formula (14) that the biological spectral reflectance can be approximated by the three basic spectral characteristics is changed to the assumed part that the biological spectral reflectance can be approximated by the four, or four or less basic spectral characteristics. Therefore, in correspondence with this, the dimension for computing the estimation matrix is changed to four from three.

According to the present embodiment, the spectral image in which blood vessel patterns are vividly displayed can be obtained as in the embodiment 1. In the present embodiment, the merit in the case of using the complementary color type color filter can be enjoyed.

Embodiments and the like configured by partially combining the above described respective embodiments also belong to the present invention.

As described above, according to each of the embodiments, the effect of being able to adjust the tissue information at a desired deep portion of a biological tissue based on the spectral image obtained by signal processing to image information in a color tone suitable for observation is obtained.

In the respective embodiments described above, the light source units 41 and 41B and the like disposed in the endoscope apparatus main body 105 are described as illumination units, but the present invention is not limited to them, and as the illumination unit, a configuration in which an LED (light emitting diode) is provided at a distal end of the endoscope 101, for example, may be adopted.

As above, according to the respective embodiments of the present invention, a spectral signal with higher precision or reliability can be obtained.

The present invention is not limited to the above described respective embodiments, but various modifications, changes and the like can be made in the range without departing from the spirit of the present invention.

Industrial Applicability

A spectral image in a narrow band as well as an ordinary image can be obtained by irradiating illumination light in a wide band, and blood vessel running patterns and the like near the surface and at a deeper portion side of a biological tissue can be observed in a visible state.

The present application is based upon and claims the benefit of priority from the prior Japanese Patent Application No. 2005-138929 filed in Japan on May 11, 2005; the prior Japanese Patent Application No. 2005-138930 filed in Japan on May 11, 2005; and the prior Japanese Patent Application No. 2005-141539 filed in Japan on May 13, 2005. The entire content of these priority applications is incorporated in the Description and Claims of the present application by reference.

The invention claimed is:

1. A signal processing device for a biological observation apparatus comprising a signal processing control unit for photoelectrically converting light reflected from a living body that is a test subject based on illumination light from an illumination unit that irradiates light to the living body, controlling an operation of an image pickup unit creating an image pickup signal, and outputting the image pickup signal to a display device, the signal processing device comprising:
a spectral signal creating section for creating a first spectral signal corresponding to when illumination or image pickup is performed in a wavelength band centered on a range from 400 nm to 440 nm, and a second spectral signal corresponding to when illumination or image pickup is performed in a wavelength band centered on a range from 520 nm to 560 nm by performing computation processing using a predetermined coefficient for spectral signal creation corresponding to an image in a narrow band of an optical wavelength based on the image pickup signal; and
a color adjusting section for adjusting a color tone for each of a plurality of wavelength bands forming the spectral signal when outputting the spectral signal to the display device, the color adjusting section configured to output the first spectral signal corresponding to when illumination or image pickup is performed in the wavelength band centered on the range from 400 nm to 440 nm to B and G channels of the display device, and to output the second spectral signal corresponding to the when illumination or image pickup is performed in the wavelength band centered on the range from 520 nm to 560 nm to an R channel of the display device.

2. The signal processing device for a biological observation apparatus according to claim 1,
wherein the spectral signal creating section creates the spectral signal by electronic circuit processing.

3. The signal processing device for a biological observation apparatus according to claim 1,
wherein the spectral signal creating section creates the spectral signal by numeric data processing.

4. The signal processing device for a biological observation apparatus according to claim 1,
wherein the spectral signal creating section uses coefficients calculated based on spectral characteristics of at least one of the illumination unit and the image pickup unit.

5. The signal processing device for a biological observation apparatus according to claim 1,
wherein the spectral signal creating section uses a coefficient calculated based on a reflection characteristic of the test subject.

6. The signal processing device for a biological observation apparatus according to claim 1,
wherein the spectral signal includes a negative signal.

7. The signal processing device for a biological observation apparatus according to claim 1,
wherein calculation of coefficients used for creation of the spectral signal is performed on assumption that the spectral characteristic of the test subject can be approximated by a linear sum of a plurality of basic spectral characteristics.

8. The signal processing device for a biological observation apparatus according to claim 7,
wherein a number of the basic spectral characteristics is a number of color separations of the reflected light or less.

9. The signal processing device for a biological observation apparatus according to claim 7,
wherein the basic spectral characteristics are calculated by performing main component analysis or orthogonal expansion for a set of spectral characteristic data of the test subject.

10. The signal processing device for a biological observation apparatus according to claim 1,
wherein calculation of coefficients used for creation of the spectral signal is performed on assumption that each of a spectral characteristic of the test subject, a spectral characteristic of the illumination unit and a spectral characteristic of an image pickup unit can be approximated by one numeric value within a predetermined wavelength band width.

11. The signal processing device for a biological observation apparatus according to claim 1,
wherein the color adjusting section performs predetermined output adjustment for a plurality of the spectral signals and outputs a plurality of the spectral signals to a B, G and R color channels of a display output section in order of wavelength, the shortest wavelength first.

12. The signal processing device for a biological observation apparatus according to claim 1,
wherein the color adjusting section performs signal conversion so that a channel including test subject information desired to be outputted with a highest contrast among a plurality of the spectral signals is reproduced as luminance in a display output device.

13. The signal processing device for a biological observation apparatus according to claim 1,
wherein the color adjusting section performs adjustment output so that a characteristic of the test subject is reproduced in a predetermined target color in a display output device.

14. The signal processing device for a biological observation apparatus according to claim 1,
wherein the test subject has at least one of a blood vessel and a mucosal microstructure.

15. The signal processing device for a biological observation apparatus according to claim 1,
wherein the biological observation apparatus is an electronic endoscope apparatus.

16. The signal processing device for a biological observation apparatus according to claim 1,
wherein the image pickup signal is created by passing through a color separating section.

17. The signal processing device for a biological observation apparatus according to claim 1,
wherein the image pickup unit is included in an endoscope.

18. The signal processing device for a biological observation apparatus according to claim 17,
wherein the endoscope is a flexible endoscope.

19. The signal processing device for a biological observation apparatus according to claim 17,
wherein the endoscope is a rigid endoscope.

20. The signal processing device for a biological observation apparatus according to claim 1,
wherein the image pickup unit is included in an oral camera.

21. The signal processing device for a biological observation apparatus according to claim 1,
wherein the image pickup unit is included in a camera picking up an image of the living body in a state in which the image pickup unit is in contact with a surface of the living body.

22. The signal processing device for a biological observation apparatus according to claim 16, wherein the color separating section is a color filter provided at the image pickup unit.

23. The signal processing device for a biological observation apparatus according to claim 16,
wherein the color separating section is a color filter provided at the illumination unit.

24. The signal processing device for a biological observation apparatus according to claim 16,
wherein primary colors of the color separating section are RGB primary colors.

25. The signal processing device for a biological observation apparatus according to claim 16,
wherein primary colors of the color separating section include CMY complementary colors.

26. A biological observation apparatus photoelectrically converting light reflected from a living body based on illumination light irradiated to the living body that is a test subject, controlling an operation of an image pickup unit creating an image pickup signal in a wide band, and outputting the image pickup signal to a display device, the biological observation apparatus comprising:
a spectral signal creating section for creating a first spectral signal corresponding to when illumination or image pickup is performed in a wavelength band centered on a range from 400 nm to 440 nm and a second spectral signal corresponding to when illumination or image pickup is performed in a wavelength band centered on a range from 520 nm to 560 nm by performing computation processing using a predetermined coefficient for spectral signal creation corresponding to an image in a narrow band of an optical wavelength based on the image pickup signal;
a color adjusting section for adjusting a color tone for each of a plurality of wavelength bands for forming the spectral signal when outputting the spectral signal to the display device, the color adjusting section configured to output the first spectral signal corresponding to when illumination or image pickup is performed in the wavelength band centered on 400 nm to 440 nm to B and G channels of the display device and to output the second spectral signal corresponding to when illumination or image pickup is performed in the wavelength band centered on 520 nm to 560 nm to an R channel of the display device; and
a plurality of light sources for emitting a plurality of illumination lights differing in spectral characteristic from each other as the illumination light.

27. The biological observation apparatus according to claim 26, further comprising a signal processing control section including the spectral signal creating section and the color adjusting section,
wherein the signal processing control section performs control of determining which one of the plurality of light sources is used for the illumination light.

28. The biological observation apparatus according to claim 26,
wherein the spectral signal creating section creates a plurality of illumination lights having desired spectral characteristics from a plurality of the light sources.

29. The biological observation apparatus according to claim 26,
wherein at least one of a plurality of light sources is a semiconductor light source.

30. The biological observation apparatus according to claim 26,
wherein at least one of a plurality of light sources has a bright line spectrum.

31. The biological observation apparatus according to claim 26,
wherein the biological observation apparatus comprises an ordinary image observation mode for performing an ordinary image observation based on the image pickup signal and a spectral image observation mode for performing a spectral image observation based on the image pickup signal,
the spectral signal creating section creating spectral signals corresponding to images in a plurality of narrow bands of optical wavelengths by signal processing based on the image pickup signal in the spectral image observation mode, and
the biological observation apparatus further comprises a light source control section for controlling a first light source of the plurality of light sources to emit the illumination light in the ordinary image observation mode and controlling the first light source and a second light source of the plurality of light sources to emit the illumination light in the spectral image observation mode, the second light source having irradiation intensity in a predetermined wavelength band higher than irradiation intensity in the wavelength bands of the other of the plurality of light sources.

* * * * *